(12) United States Patent
Harper et al.

(10) Patent No.: US 12,275,941 B2
(45) Date of Patent: Apr. 15, 2025

(54) PRODUCTS AND METHODS FOR INHIBITION OF EXPRESSION OF DYNAMIN-1 VARIANTS

(71) Applicants: RESEARCH INSTITUTE AT NATIONWIDE CHILDREN'S HOSPITAL, Columbus, OH (US); THE TRUSTEES OF COLUMBIA UNIVERSITY IN THE CITY OF NEW YORK, New York, NY (US)

(72) Inventors: Scott Quenton Harper, Powell, OH (US); Wayne N. Frankel, Katonah, NY (US)

(73) Assignees: RESEARCH INSTITUTE AT NATIONWIDE CHILDREN'S HOSPITAL, Columbus, OH (US); THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 162 days.

(21) Appl. No.: 17/231,963

(22) Filed: Apr. 15, 2021

(65) Prior Publication Data

US 2022/0333115 A1 Oct. 20, 2022

(51) Int. Cl.
| | | |
|---|---|---|
| *C12N 15/113* | (2010.01) | |
| *A61K 31/713* | (2006.01) | |
| *C12N 15/86* | (2006.01) | |

(52) U.S. Cl.
CPC ........ *C12N 15/1138* (2013.01); *A61K 31/713* (2013.01); *C12N 15/86* (2013.01); *C12N 2310/14* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,173,414 A | 12/1992 | Lebkowski et al. | |
| 5,658,776 A | 8/1997 | Flotte et al. | |
| 5,786,211 A | 7/1998 | Johnson | |
| 5,871,982 A | 2/1999 | Wilson et al. | |
| 6,258,595 B1 | 7/2001 | Gao et al. | |
| 6,566,118 B1 | 5/2003 | Atkinson et al. | |
| 8,668,927 B2 | 3/2014 | Reiser et al. | |
| 9,434,928 B2 | 9/2016 | Mendell et al. | |
| 10,865,414 B2 | 12/2020 | Freier | |
| 10,947,540 B2 | 3/2021 | Bitoun et al. | |
| 11,345,913 B2 * | 5/2022 | Harper | C12N 15/113 |
| 2007/0197438 A1 | 8/2007 | Reiser et al. | |
| 2011/0081362 A1 * | 4/2011 | Elledge | A61P 35/00 514/249 |
| 2019/0136235 A1 * | 5/2019 | Harper | C12N 7/00 |
| 2020/0131172 A1 | 4/2020 | Ji et al. | |
| 2021/0095291 A1 | 4/2021 | Buj Bello | |

FOREIGN PATENT DOCUMENTS

| | | |
|---|---|---|
| WO | WO-95/13365 A1 | 5/1995 |
| WO | WO-95/13392 A1 | 5/1995 |
| WO | WO-96/17947 A1 | 6/1996 |
| WO | WO-97/06243 A1 | 2/1997 |
| WO | WO-97/08298 A1 | 3/1997 |
| WO | WO-97/09441 A2 | 3/1997 |
| WO | WO-97/21825 A1 | 6/1997 |
| WO | WO-98/09657 A2 | 3/1998 |
| WO | WO-99/11764 A2 | 3/1999 |
| WO | WO-01/83692 A2 | 11/2001 |
| WO | WO-02/053703 A2 | 7/2002 |

OTHER PUBLICATIONS

Dayton et al. The advent of AAV9 expands applications for brain and spinal cord gene delivery. Expert Opin Biol Ther. Jun. 2012 ;12(6): 757-766. (Year: 2012).*
Gholizadeh et al. Transduction of the central nervous system after intracerebroventricular injection of adeno-associated viral vectors in neonatal and juvenile mice. Hum Gene Ther Methods. Aug. 2013;24(4):205-13. Epub Aug. 3, 2013. (Year: 2013).*
Aimiuwu et al. Modeling Gene Specific Therapy of DNM1 Epileptic Encephalopathy [abstract]. In: American Epilepsy Society meeting. Nov. 5, 2018. Abstract nr 1.116. (Year: 2018).*
Nidetz et al. Adeno-associated viral vector-mediated immune responses: Understanding barriers to gene delivery. Pharmacology & Therapeutics. 207 (2020) 107453. Epub Dec. 11, 2019. (Year: 2019).*
Colasante et al. dCas9-Based Scn1a Gene Activation Restores Inhibitory Interneuron Excitability and Attenuates Seizures in Dravet Syndrome Mice. Molecular Therapy. Jan. 8, 2020; (28) 1: 235-253. (Year: 2020).*
Nationwide Children's Hospital (n.d.). Vector Production Process. Research. https://www.nationwidechildrens.org/research/resources-infrastructure/innovation-and-technology/gmp-facility/vector-production-process (Year: 2023).*
Iodice R, Ugga L, Aruta F, Iovino A, Ruggiero L. Facioscapulohumeral muscular dystrophy (FSHD) and multiple sclerosis: a case report. Acta Myol. Mar. 1, 2020;39(1):29-31. doi: 10.36185/2532-1900-005. PMID: 32607477; PMCID: PMC7315893. (Year: 2020).*
Aimiuwu et al., "RNAi-Based Gene Therapy Rescues Developmental and Epileptic Encephalopathy in a Genetic Mouse Model," Mol. Ther., 28(7):1706-1716 (2020).
Asinof et al., "Dynamin 1 isoform roles in a mouse model of severe childhood epileptic encephalopathy," Neurobiol. Dis., 95:1-11 (2016).

(Continued)

*Primary Examiner* — Allison M Fox
*Assistant Examiner* — Alyssa G Weston
(74) *Attorney, Agent, or Firm* — MARSHALL, GERSTEIN & BORUN LLP

(57) ABSTRACT

RNA interference-based methods and products for inhibiting the expression of pathogenic dynamin-1 variants are provided. Delivery vehicles such as recombinant adeno-associated viruses deliver DNAs encoding RNAs that inhibit the expression of the dynamin-1 variants. The methods treat, for example, developmental and epileptic encephalopathies.

25 Claims, 12 Drawing Sheets
(12 of 12 Drawing Sheet(s) Filed in Color)
Specification includes a Sequence Listing.

(56) References Cited

OTHER PUBLICATIONS

Asinof et al., "Independent Neuronal Origin of Seizures and Behavioral Comborbidities in an Animal Model of a Severe Childhood Genetic Epileptic Encephalopathy," PLOS Genet., 11:e1005347 (2015).
Boudreau et al., "Rapid Cloning and Validation of MicroRNA Shuttle Vectors: A Practical Guide," Chapter 2 of Harper (Ed.), RNA Interference Techniques, Neuromethods, vol. 58, Springer Science Business Media, LLC (2011).
Boumil et al., "A Missense Mutation in a Highly Conserved Alternate Exon of Dynamin-1 Causes Epilepsy in Fitful Mice," PLoS Genet., 6:e1001046 (2010).
Brereton et al., "Mutations in the PH Domain of DNM1 are associated with a nonepileptic phenotype characterized by developmental delay and neurobehavioral abnormalities," Mol. Genet. Genomic Med., 6:294-300 (2018).
Buono et al., "Reducing dynamin 2 (DNM2) rescues DNM2-related dominant centronuclear myopathy, " PNAS, 115(43):11066-11071 (2018).
Carter, "Adeno-associated virus vectors," Current Opinions in Biotechnology, 3:533-539 (1992).
Choudhury et al., "In Vivo Selection Yields AAV-B1 Capsid for Central Nervous System and Muscle Gene Therapy," Mol. Ther., 24(7):1247-1257 (2016).
Clark et al., "Highly Purified Recombinant Adeno-Associated Virus Vectors are Biologically Active and Free of Detectable Helper and Wild-Type Viruses," Hum. Gene Ther., 10(6):1031-1039 (1999).
Clark et al., Gene Ther., "A Stable cell line carrying adenovirus-inducible rep and cap genes allows for infectivity titration of adeno-associated virus vectors," 3:1124-1132 (1996).
Clinical Trial #: NCT03650452—Aug. 28, 2018.
Clinical Trial #: NCT04033159—Jul. 25, 2019.
Clinical Trial #: NCT04442295—Jun. 22, 2020.
Consortium, "De Novo Mutations in Synaptic Transmission Genes Including DNM1 Cause Epileptic Encephalopathies," Am. J. Hum. Genet., 100:179 (2017).
Davidson et al., "Current prospects for RNA interference-based therapies," Nat. Rev. Genet., 12:329-40 (2011).
De et al., "High Levels of Persistent Expression of α1-Antitrypsin Mediated by the Nonhuman Primate Serotype rh. 10 Adeno-associated Virus Despite Preexisting Immunity to Common Human Adeno-associated Viruses," Mol. Ther., 13(1): 67-76 (2006).
Dhindsa et al., "Epileptic encephalopathy-causing mutations in DNM1 impair synaptic vesicle endocytosis," Neurol. Genet., 1:e4, 10 pages (2015).
Diling et al., "Circular RNA NF1-419 enhances autophagy to ameliorate senile dementia by binding Dynamin-1 and Adaptor protein 2 B1 in AD-like mice," Aging, 11(24):12002-12031 (2019).
Gao et al., "Clades of Adeno-Associated Viruses Are Widely Disseminated in Human Tissues," J. Virol., 78:6381-6388 (2004).
Harper, "Progress and Challenges in RNA Interference Therapy for Huntington Disease," Arch. Neurol., 66:933-938 (2009).
Hermonat et al., "Use of adeno-associated virus as a mammalian DNA cloning vector: Transduction of neomycin resistance into mammalian tissue culture cells," Proc. Natl. Acad. Sci. USA, 81:6466-6470 (1984).
Kolnikova et al., "DNM1 encephalopathy—atypical phenotype with hypomyelination due to a novel de novo variant in the DNM1 gene," Seizure, 56:31-33 (2018).
Kunkel et al., "Analysis of deletions in DNA from patients with Becker and Duchenne muscular dystrophy," Nature, 322(6074):73-77 (1986).
Kunkel et al., "Upstream elements required for efficient transcription of a human U6 RNA gene resemble those of U1 and U2 genes even though a different polymerase is used," Genes Dev. 2(2):196-204 (1988).
Laughlin et al., "Cloning of infectious adeno-associated virus genomes in bacterial plasmids," Gene, 23:65-73 (1983).
Lebkowski et al., "Adeno-Associated Virus: a Vector System for Efficient Introduction and Integration of DNA into a Variety of Mammalian Cell Types," Mol. Cell. Biol., 8(10:3988-3996 (1988).
Li et al., "Clinical Assessments and EEG Analyses of Encephalopathies Associated with Dynamin-1 Mutation," Front. Pharmacol., 10:1454, 10 pages (2019).
Marsic et al., "Vector Design Tour de Force: Integrating Combinatorial and Rational Approaches to Derive Novel Adeno-associated Virus Variants," Molecular Therapy 22(11):1900-1909 (2014).
McCarty, "Self-complementary AAV Vectors; Advances and Applications," Mol. Ther., 16(10):1648-1656 (2008).
McLaughlin et al., "Adeno-Associated Virus General Transduction Vectors: Analysis of Proviral Structures," J. Virol., 62:1963-1973 (1988).
Morelli et al., "Allelle-specific RNA interference prevents neuropathy in Charcot-Marie-Tooth disease type 2D mouse models," J Clin Invest. 129(12):5568-83 (2019).
Mori et al., "Two novel adeno-associated viruses from cynomolgus monkey: pseudotyping characterization of capsid protein," Virology 330(2):375-383 (2004).
Muzyczka, "Use of Adeno-Associated Virus as a General Transduction Vector for Mammalian Cells," Curr. Topics in Microbiol. and Immunol., 158:97-129 (1992).
Paddison et al., "Stable suppression of gene expression by RNAi in mammalian cells," Proc. Natl. Acad. Sci. USA, 99(3):1443-1448 (2002).
Paul et al., "Increased Viral Titer Through Concentration of Viral Harvests from Retroviral Packaging Lines," Hum. Gene Ther., 4:609-615 (1993).
Paule et al., "Transcription by RNA polymerases I and III," Nuc. Acids Res., 28(6):1283-1298 (2000).
Perrin et al., "An experimental rabies vaccine produced with a new BHK-21 suspension cell culture process: use of serum-free medium and perfusion-reactor system," Vaccine, 13:1244-1250 (1995).
Samulski et al., "Cloning of adeno-associated virus into pBR322: Rescue of intact virus from the recombinant plasmid in human cells," Proc. Natl. Acad. S6. USA, 79:2077-2081 (1982).
Samulski et al., "Helper-Free Stocks of Recombinant Adeno-Associated Viruses: Normal Integration Does Not Require Viral Gene Expression," J. Virol., 63:3822-3828 (1989).
Schenpp et al., "Highly Purified Recombinant Adeno-Associated Virus Vectors," Methods Mol. Med., 69: 427-443 (2002).
Senapathy et al., "Molecular Cloning of Adeno-associated Virus Variant Genomes and Generation of Infectious Virus by Recombination in Mammalian Cells," J. Biol. Chem., 259(7):4661-4666 (1984).
Tasfaout et al., "Antisense oligonucleotide-mediated Dnm2 knockdown prevents and reverts myotubular myopathy in mice," Nature Communications, vol. 8—Article 15661 (2017).
Tratschin et al., "A Human Parvovirus, Adeno-Associated Virus, as a Eucaryotic Vector: Transient Expression and Encapsidation of the Procaryotic Gene for Chloramphenicol Acetyltransferase," Mol. Cell. Biol. 4(10):2072-2081 (1984).
Tratschin et al., "Adeno-Associated Virus Vector for High-Frequency Integration, Expression, and Rescue of Genes in Mammalian Cells," Mol. Cell. Biol. 5: 3251-3260 (1985).
Trochet et al., "Allele-specific silencing therapy for Dynamin 2-related dominant centronuclear myopathy," EMBO Mol Med, 10(2):239-253 (2018).
Von Spiczak et al., "DNM1 encephalopathy," Neurology, 89:385-394 (2017).
Wallace et al., "RNa Interference Inhibits DUX4-induced Muscle Toxicity In Vivo: Implications for a Targeted FSHD Therapy," Mol. Ther. J. Am. Soc. Gene Ther., 20:1417-1423 (2012).
Wallace et al., "RNAi Therapy for Dominant Muscular Dystrophies and other Myopathies," Duan (Ed.), Section 7.3 of Chapter 7 in Muscle Gene Therapy, Springer Science Business Media, LLC, pp. 99-115 (2010).
International Search Report and Written Opinion from International Application No. PCT/US22/24885 mailed Jan. 6, 2023.

(56) References Cited

OTHER PUBLICATIONS

Nidetz et al., "Adeno-associated viral vector-mediated immune responses: Understanding barriers to gene delivery," Pharmacology & Therapeutics, 207, 13 pages (2020).

* cited by examiner

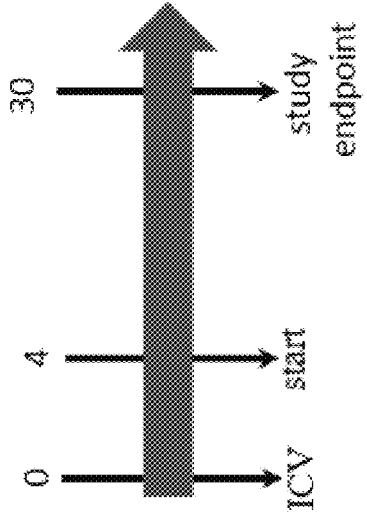
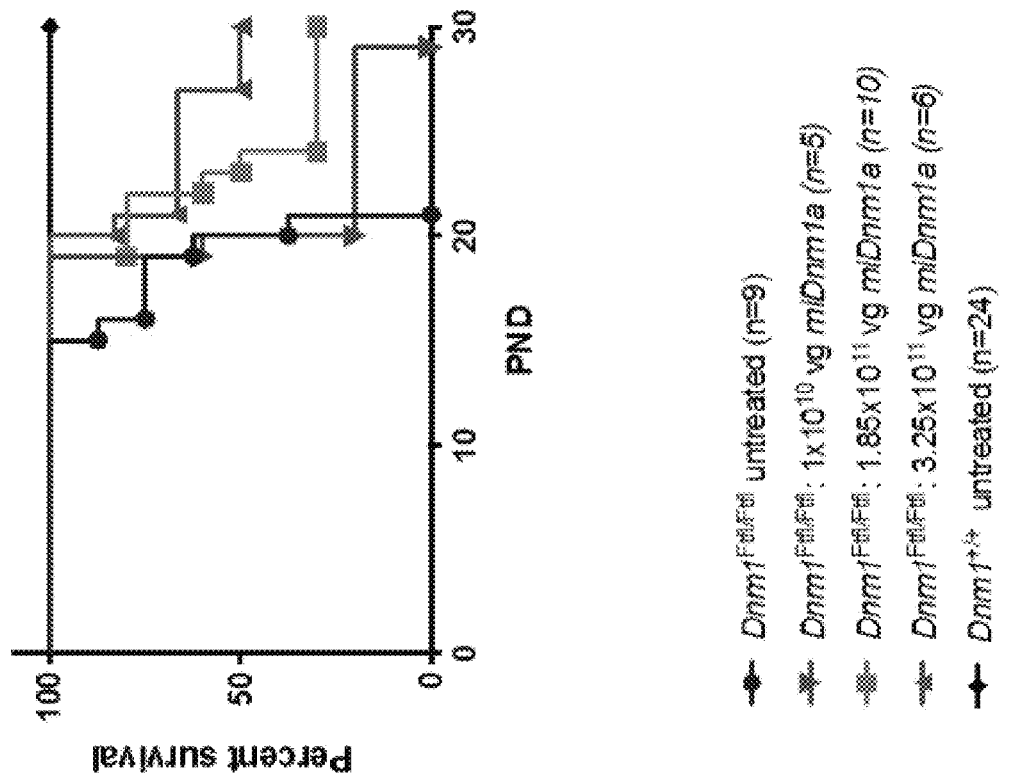
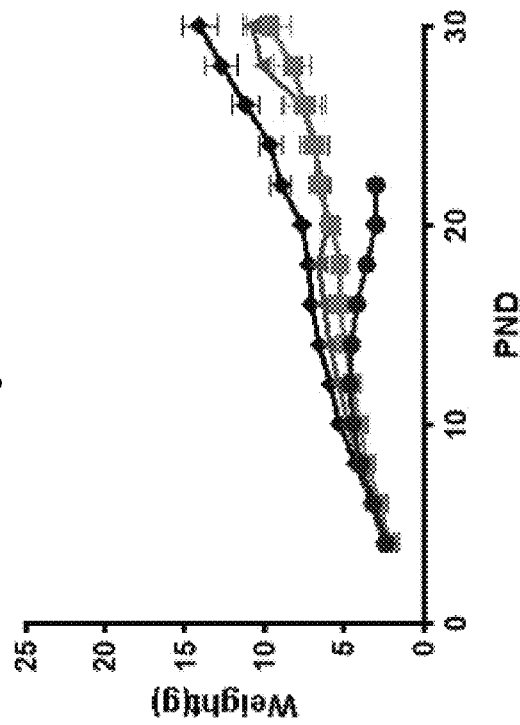

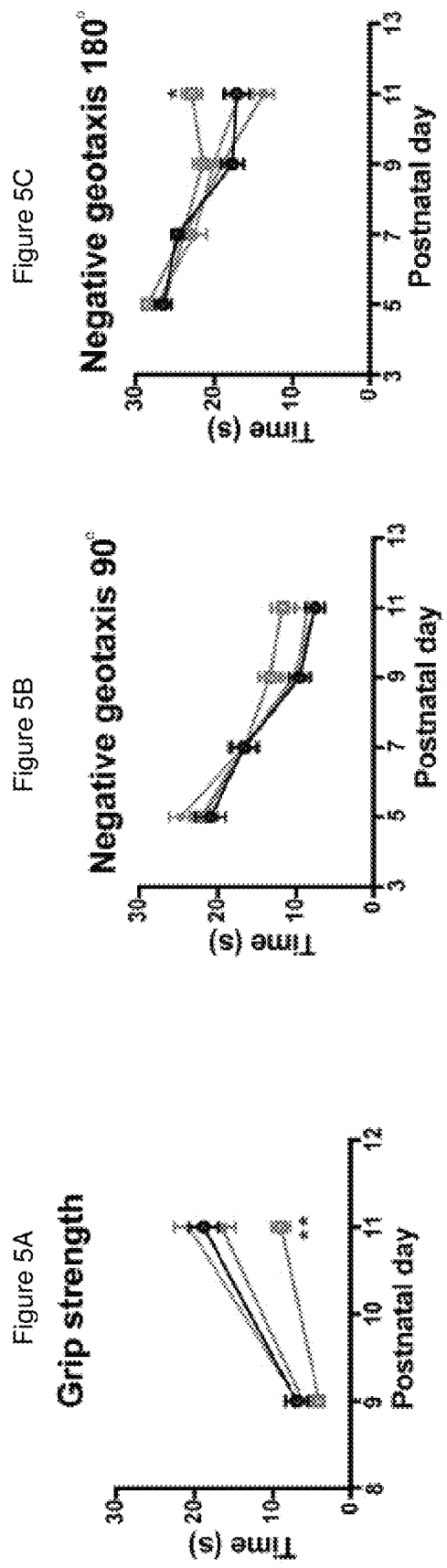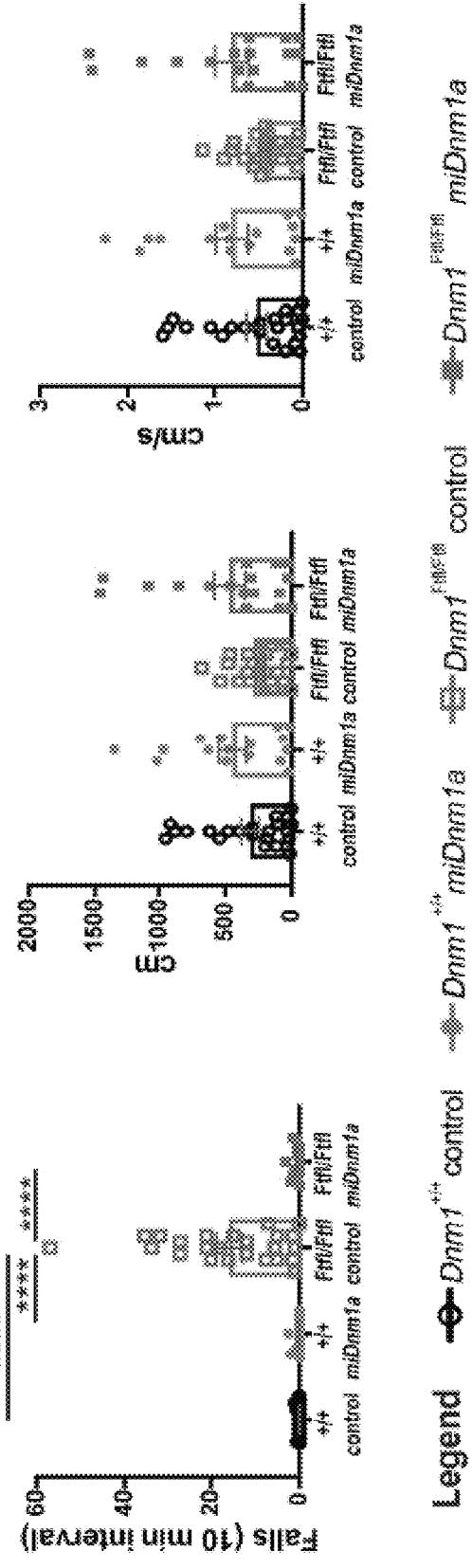
Figure 5A Grip strength
Figure 5B Negative geotaxis 90°
Figure 5C Negative geotaxis 180°
Figure 5D Ataxia
Figure 5E Locomotion
Figure 5F Speed

PRODUCTS AND METHODS FOR INHIBITION OF EXPRESSION OF DYNAMIN-1 VARIANTS

STATEMENT OF U.S. GOVERNMENT INTEREST

This invention was made with government support under R37 NS031348 and F31 NS111808 awarded by The National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: ASCII text file named "56694_SeqListing.txt", file size 18,907 bytes created Apr. 15, 2021.

FIELD

RNA interference-based methods and products for inhibiting the expression of pathogenic dynamin-1 variants are provided. Delivery vehicles such as recombinant adeno-associated viruses deliver DNAs encoding RNAs that inhibit expression of the dynamin-1 variants. The methods treat developmental and epileptic encephalopathies.

BACKGROUND

DNM1 encodes a critical multimeric brain-specific GTPase, dynamin-1, that localizes to the presynapse where it mediates endocytosis. Individuals with pathogenic DNM1 variants suffer from two of the most severe developmental and epileptic encephalopathy (DEE) syndromes, Lennox-Gastaut Syndrome and Infantile Spasms. The identification of affected individuals is likely to increase as DNM1 is now included on screening panels for severe childhood epilepsy. Children with DNM1 mutations suffer from intractable conditions manifesting as early-onset seizures, global developmental delay, profound intellectual disability, lack of speech, muscular hypotonia, dystonia and spasticity. Affected individuals do not respond well to anti-epileptic drugs, leaving >80% of patients with seizures, as is the case with many DEEs.

Prior to the identification of pathogenic human variants, the first direct link between DNM1 and severe epilepsy was a spontaneous missense mutation in the mouse orthologue, termed "fitful" (gene symbol: $Dnm1^{Ftfl}$) [Boumil et al., PLoS Genet., 6: e1001046 (2010)]. This mutation occurs in a mutually-exclusive alternate exon in the middle domain of Dnm1 that defines Dnm1a—which along with Dnm1b comprises two functionally semi-redundant isoforms of Dnm1. Peptides encoded by these very highly conserved exons form part of the assembly domain that is critical for oligomerization of dynamin monomers into ring structures that carry out endocytosis [von Spiczak et al., Neurology, 89: 385-394 (2017) and Boumil, supra].

Whereas $Dnm1^{Ftfl/+}$ heterozygous mice show only mild spontaneous and handling-induced seizures from 2 to 3 months of age and have a normal lifespan, $Dnm1^{Ftfl/Ftfl}$ homozygotes show a DEE-like phenotype with severe ataxia, developmental delay, and fully penetrant lethal seizures by the end of the third postnatal week. While Dnm1b is expressed predominantly during gestation and expression wanes during early postnatal development, Dnm1a expression increases during early postnatal development and peaks during the second postnatal week, becoming the predominant isoform of adulthood. However, neither Dnm1a nor Dnm1b isoform-specific homozygous knockout mice ($Dnm1^{\Delta a/\Delta a}$ or $Dnm1^{\Delta b/\Delta b}$) show seizures or other overt phenotypic characteristics associated with the $Dnm1^{Ftfl}$ allele [Asinof et al., PLoS Genet., 11: e1005347 (2015) and Asinof et al., Neurobiol. Dis., 95: 1-11 (2016)]. These and other in vivo and in vitro studies suggest that $Dnm1^{Ftfl}$ exerts a dominant-negative effect on protein function, as was modeled or predicted for all DNM1 pathogenic variants [Dhindsa et al., Neurol. Genet., 1: e4 (2015); Asinof (2016), supra; and von Spiczak, supra].

Treatment of DEEs is currently limited to treatment of symptoms, primarily by use of antiepileptic drugs. The drugs do not address the underlying genetic defect and thus offer no hope of stopping or slowing disease progression and, when given for long durations, can result in loss of efficacy.

There thus exists a need in the art for products and methods for treatment of DEEs.

SUMMARY

The disclosure herein provides methods to specifically induce silencing of deleterious DNM1 isoforms by RNA interference (RNAi) using vectors expressing artificial inhibitory RNAs targeting the DMN1 mRNA. The artificial DMN1 inhibitory RNAs contemplated include, but are not limited to, small interfering RNAs (siRNAs) (also referred to as short interfering RNAs, small inhibitory RNAs or short inhibitory RNAs), short hairpin RNAs (shRNAs) and miRNA shuttles (artificial miRNAs) that inhibit expression of pathgenic DNM1 isoforms. The artificial inhibitory RNAs are referred to as miDNM1s herein. The miDNM1s are small regulatory sequences that act post-transcriptionally by targeting, for example, a coding region or 3'UTR of DNM1 mRNA in a reverse complementary manner resulting in reduced DNM1 mRNA and protein levels. Use of the methods and products is indicated, for example, in preventing or treating DEE.

DNM1 inhibitory RNAs are provided as well as polynucleotides encoding one or more of the RNAs. Exemplary DNM1 inhibitory RNAs provided are miRNAs that target Dnm1a, the isoform which houses $Dnm1^{Ftfl}$. Other exemplary inhibitory RNAs provided target human DNM1a and DNM1b isoforms, which differ in an alternatively-spliced DNM1 exon 10, called 10a and 10b.

Provided herein are the following exemplary miRNAs and sequences.

| | | | MicroRNAs targeting mouse and human exon 10a sequences | | |
|---|---|---|---|---|---|
| Full-length mouse miRNA sequence (DNA encoding sequence, 5' to 3') | Full-length mouse miRNA sequence (RNA sequence, 5' to 3') | Mature antisense guide strand sequence (5' to 3') | Binding site on human DNM1 exon 10a (SEQ ID NO: 52) | Mis-matches with DNM1 exon 10b | Name |
| CTCGAGTGAGCGAT GTGTGGACATGGTA GTCAGTCTGTAAAG | CUCGAGUGAGCGA UGUGUGGACAUGG UAGUCAGUCUGUA | ACUGACUACC AUGUCCACAC AC | 82-103 | 5 | miDNM1a-1 |

| | | | | | |
|---|---|---|---|---|---|
| CCACAGATGGGACT GACTACCATGTCCA CACACTGCCTACTA GA (SEQ ID NO: 1) | AAGCCACAGAUGG GACUGACUACCAU GUCCACACACUGC CUACUAGA (SEQ ID NO: 18) | (SEQ ID NO: 35) | | | |
| CTCGAGTGAGCGAA CCATCAGAAAGTGT AGTGAACTGTAAAG CCACAGATGGGTTC ACTACACTTTCTGA TGGTGTGCCTACTA GA (SEQ ID NO: 2) | CUCGAGUGAGCGA ACCAUCAGAAAGU GUAGUGAACUGUA AAGCCACAGAUGG GUUCACUACACUU UCUGAUGGUGUGC CUACUAGA (SEQ ID NO: 19) | UUCACUACAC UUUCUGAUGG UG (SEQ ID NO: 36) | 115-136 with single mismatch at human DNM1 exon 10a position 133 | 5 | miDNM1a-4 |

| MicroRNAs designed to target human DNM1 exon 10a | | | | | |
|---|---|---|---|---|---|
| Full-length human miRNA sequence (DNA encoding sequence, 5' to 3') | Full-length human miRNA sequence (RNA sequence, 5' to 3') | Mature antisense guide strand sequence (5' to 3') | Binding site on human DNM1 exon 10a (SEQ ID NO: 52) | Mis-matches with DNM1 exon 10b | Name |
| CTCGAGTGAGCGAA CCATCAGAAAGTGT AGCGAACTGTAAAG CCACAGATGGGTTC GCTACACTTTCTGA TGGTGTGCCTACTA GA (SEQ ID NO: 3) | CUCGAGUGAGCGAA CCAUCAGAAAGUGU AGCGAACUGUAAAG CCACAGAUGGGUUC GCUACACUUUCUGA UGGUGUGCCUACUA GA (SEQ ID NO: 20) | UUCGCUACAC UUUCUGAUGG UG (SEQ ID NO: 37) | 115-136 | 4 | Humanized miDNM1-10a-4 |
| CTCGAGTGAGCGAC CAGTATCAAGTGTG TGGATACTGTAAAG CCACAGATGGGTAT CCACACACTTGATA CTGGGTGCCTACTA GA (SEQ ID NO: 4) | CUCGAGUGAGCGAC CAGUAUCAAGUGUG UGGAUACUGUAAAG CCACAGAUGGGUAU CCACACACUUGAUA CUGGGUGCCUACUA GA (SEQ ID NO: 21) | UAUCCACAC ACUUGAUAC UGGG (SEQ ID NO: 38) | 71-92 | 4 | miDNM1-10a-71 |
| CTCGAGTGAGCGAC AGTATCAAGTGTGT GGATATCTGTAAAG CCACAGATGGGATA TCCACACACTTGAT ACTGGTGCCTACTA GA (SEQ ID NO: 5) | CUCGAGUGAGCGAC AGUAUCAAGUGUGU GGAUAUCUGUAAAG CCACAGAUGGGAUA UCCACACACUUGAU ACUGGUGCCUACUA GA (SEQ ID NO: 22) | AUAUCCACAC ACUUGAUACU GG (SEQ ID NO: 39) | 72-93 | 4 | miDNM1-10a-72 |
| CTCGAGTGAGCGAA GCTCACAGCCACCA TCAGAACTGTAAAG CCACAGATGGGTTC TGATGGTGGCTGTG AGCTCTGCCTACTA GA (SEQ ID NO: 6) | CUCGAGUGAGCGAA GCUCACAGCCACCA UCAGAACUGUAAAG CCACAGAUGGGUUC UGAUGGUGGCUGUG AGCUCUGCCUACUA GA (SEQ ID NO: 23) | UUCUGAUGGU GGCUGUGAGC UC (SEQ ID NO: 40) | 104-125 | 4 | miDNM1-10a-104 |
| CTCGAGTGAGCGAC TCACAGCCACCATC AGAAAGCTGTAAAG CCACAGATGGGCTT TCTGATGGTGGCTG TGAGCTGCCTACTA GA (SEQ ID NO: 7) | CUCGAGUGAGCGAC UCACAGCCACCAUC AGAAAGCUGUAAAG CCACAGAUGGGCUU UCUGAUGGUGGCUG UGAGCUGCCUACUA GA (SEQ ID NO: 24) | CUUUCUGAUG GUGGCUGUGA GC (SEQ ID NO: 41) | 106-127 | 4 | miDNM1-10a-106 |

MicroRNAs designed to target human DNM1 exon 10b

| Full-length human miRNA sequence (DNA encoding sequence, 5' to 3') | Full-length human miRNA sequence (RNA sequence, 5' to 3') | Mature antisense guide strand sequence (5' to 3') | Binding site on human DNM1 exon 10b (SEQ ID NO: 53) | Mis-matches with DNM1 exon 10a | Name |
|---|---|---|---|---|---|
| CTCGAGTGAGCGAG GGGCTGTTTACCCC AGACATCTGTAAAG CCACAGATGGGATG TCTGGGGTAAACAG CCCCGTGCCTACTA GA (SEQ ID NO: 8) | CUCGAGUGAGCGAG GGGCUGUUUACCCC AGACAUCUGUAAAG CCACAGAUGGGAUG UCUGGGGUAAACAG CCCCGUGCCUACUA GA (SEQ ID NO: 25) | AUGUCUGGGG UAAACAGCCC CG (SEQ ID NO: 42) | 3-24 | 6 | miDNM1-10b-3 |
| CTCGAGTGAGCGCG GCCTTTGAGACCAT TGTGAACTGTAAAG CCACAGATGGGTTC ACAATGGTCTCAAA GGCCATGCCTACTA GA (SEQ ID NO: 9) | CUCGAGUGAGCGCG GCCUUUGAGACCAU UGUGAACUGUAAAG CCACAGAUGGGUUC ACAAUGGUCUCAAA GGCCAUGCCUACUA GA (SEQ ID NO: 26) | UUCACAAUGG UCUCAAAGGC CA (SEQ ID NO: 43) | 24-45 | 4 | miDNM1-10b-24 |
| CTCGAGTGAGCGAG CCTTTGAGACCATT GTGAAAC TGTAAAGCCACAGA TGGGTTTCACAATG GTCTCAAAGGCCTG CCTACTAGA (SEQ ID NO: 10) | CUCGAGUGAGCGAG CCUUUGAGACCAUU GUGAAACUGUAAAG CCACAGAUGGGUUU CACAAUGGUCUCAA AGGCCUGCCUACUA GA (SEQ ID NO: 27) | UUUCACAAUG GUCUCAAAGG CC (SEQ ID NO: 44) | 25-46 | 4 | miDNM1-10b-25 |
| CTCGAGTGAGCGACA GGTGAAGAAGATCC GAGAACTGTAAAGCC ACAGATGGGTTCTCG GATCTTCTTCACCTGC TGCCTACTAGA (SEQ ID NO: 11) | CUCGAGUGAGCGAC AGGUGAAGAAGAUC CGAGAACUGUAAAG CCACAGAUGGGUUC UCGGAUCUUCUUCA CCUGCUGCCUACUA GA (SEQ ID NO: 28) | UUCUCGGAUC UUCUUCACCU GC (SEQ ID NO: 45) | 49-70 | 4 | miDNM1-10b-49 |
| CTCGAGTGAGCGAGT GTCTCAAGTGTGTGG ACATCTGTAAAGCCA CAGATGGGATGTCCA CACACTTGAGACACG TGCCTACTAGA (SEQ ID NO: 12) | CUCGAGUGAGCGAG UGUCUCAAGUGUG UGGACAUCUGUAAA GCCACAGAUGGGAU GUCCACACACUUGA GACACGUGCCUACU AGA (SEQ ID NO: 29) | AUGUCCACAC ACU UGACA CG (SEQ ID NO: 46) | 72-93 | 3 | miDNM1-10b-72 |
| CTCGAGTGAGCGCCG GAGCTAATCAGCACC GTTACTGTAAAGCCA CAGATGGGTAACGG TGCTGATTAGCTCCG ATGCCTACTAGA (SEQ ID NO: 13) | CUCGAGUGAGCGCC GGAGCUAAUCAGCA CCGUUACUGUAAAG CCACAGAUGGGUAA CGGUGCUGAUUAGC UCCGAUGCCUACUA GA (SEQ ID NO: 30) | UAACGGUGCU GAUUAGCUCC GA (SEQ ID NO: 47) | 101-122 | 8 | miDNM1-10b-101 |
| CTCGAGTGAGCGAG GAGCTAATCAGCACC GTTAGCTGTAAAGCC ACAGATGGGCTAAC GGTGCTGATTAGCTC CGTGCCTACTAGA (SEQ ID NO: 14) | CUCGAGUGAGCGAG GAGCUAAUCAGCAC CGUUAGCUGUAAAG CCACAGAUGGGCUA ACGGUGCUGAUUAG CUCCGUGCCUACUA GA (SEQ ID NO: 31) | CUAACGGUGC UGAUUAGCUC CG (SEQ ID NO: 48) | 112-123 | 7 | miDNM1-10b-102 |
| CTCGAGTGAGCGAG AGCTAATCAGCACCG TTAGCTGTAAAGCC ACAGATGGGTCTAAC GGTGCTGATTAGCTC CTGCCTACTAGA (SEQ ID NO: 15) | CUCGAGUGAGCGAG AGCUAAUCAGCACC GUUAGACUGUAAAG CCACAGAUGGGUCU AACGGUGCUGAUUA GCUCCUGCCUACUA GA (SEQ ID NO: 32) | UCUAACGGUG CUGAUUAGCU CC (SEQ ID NO: 49) | 113-124 | 6 | miDNM1-10b-103 |

-continued

MicroRNAs designed to target human DNM1 exon 10b

| Full-length human miRNA sequence (DNA encoding sequence, 5' to 3') | Full-length human miRNA sequence (RNA sequence, 5' to 3') | Mature antisense guide strand sequence (5' to 3') | Binding site on human DNM1 exon 10b (SEQ ID NO: 53) | Mis-matches with DNM1 exon 10a | Name |
|---|---|---|---|---|---|
| CTCGAGTGAGCGCCC GTTAGACAGTGCACC AAGACTGTAAAGCCA CAGATGGGTCTTGGT GCACTGTCTAACGGT TGCCTACTAGA (SEQ ID NO: 16) | CUCGAGUGAGCGCC CGUUAGACAGUGCA CCAAGACUGUAAAG CCACAGAUGGGUCU UGGUGCACUGUCUA ACGGUUGCCUACUA GA (SEQ ID NO: 33) | UCUUGGUGC ACUGUCUAAC GGU (SEQ ID NO: 50) | 116-137 | 5 | miDNM1-10b-116 |
| CTCGAGTGAGCGAC GTTAGACAGTGCACC AAGAACTGTAAAGCC ACAGATGGGTTCTTG GTGCACTGTCTAACG GTGCCTACTAGA (SEQ ID NO: 17) | CUCGAGUGAGCGAC GUUAGACAGUGCAC CAAGAACUGUAAAG CCACAGAUGGGUUC UUGGUGCACUGUCU AACGGUGCCUACUA GA (SEQ ID NO: 34) | UUCUUGGUG CACUGUCUAA CGG (SEQ ID NO: 51) | 117-138 | 4 | miDNM1-10b-117 |

The disclosure provides nucleic acids comprising RNA-encoding template DNA sequences comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% identity to the sequence set forth in any one of SEQ ID NOs: 1-17.

Exemplary miDNM1s comprise the full length sequences set out in any one of SEQ ID NOs: 18-34 or variants thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% identity to the sequence set forth in any one of SEQ ID NOs: 18-34. Corresponding final processed antisense guide strand sequences are respectively set out in SEQ ID NOs: 35-51, or are variants thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% identity to the sequence set forth in any one of SEQ ID NOs: 35-51. The processed antisense guide strand is the strand of the mature miRNA duplex that becomes the RNA component of the RNA induced silencing complex ultimately responsible for sequence-specific gene silencing.

miDNM1s can specifically bind to a segment of a messenger RNA (mRNA) encoded by a human DNM1 gene, including but not limited to, exon 10a (SEQ ID NO: 52)

Human DNM1 exon 10a (5' to 3')
(SEQ ID NO: 52)
GACGGGCCTCTTCACACCTGACCTCGCTTTTGAAGCCACAGTGAAAAG

CAGGTGCAGAAGCTCAAAGAGCCCAGTATCAAGTGTGTGGATATGGTAG

TCAGTGAGCTCACAGCCACCATCAGAAAGTGTAGCGAAAAG
or exon 10b

Human DNM1 exon 10b (5' to 3')
(SEQ ID NO: 53)
AACGGGGCTGTTTACCCCAGACATGGCCTTTGAGACCATTGTGAAAAAG

CAGGTGAAGAAGATCCGAGAACCGTGTCTCAAGTGTGTGGACATGGTTA

TCTCGGAGCTAATCAGCACCGTTAGACAGTGCACCAAGAAG of the human DNM1 gene, wherein the segment is conserved relative to mRNA encoded by the wild-type mouse DNM1 gene, including but not limited to, exon 10a (SEQ ID NO: 54)

Mouse Dnm1 exon 10a (5' to 3')
(SEQ ID NO: 54)
GACGGGCCTCTTCACACCTGACCTCGCTTTTGAAGCCACAGTGAAAAAG

CAGGTGCAGAAGCTCAAAGAGCCCAGTATCAAGTGTGTGGACATGGTAG

TCAGTGAACTCACGTCCACCATCAGAAAGTGTAGTGAAAA
or exon 10b (SEQ ID NO: 55)

Mouse Dnm1 exon 10b (5' to 3')
(SEQ ID NO: 55)
AACGGGGCTCTTTACCCCAGACATGGCCTTTGAAACCATTGTGAAAAAG

CAGGTGAAGAAGATTCGAGAGCCGTGTCTCAAGTGTGTGGACATGGTTA

TCTCGGAGCTAATCAGCACGGTTAGACAGTGCACCAAGAAG of the mouse DNM1 gene, respectively. For example, a miDNM1 can specifically bind a mRNA segment that is complementary to a sequence within nucleotides 115-136 of SEQ ID NO: 52.

Delivery of DNA encoding miDNM1s can be achieved using a delivery vehicle that delivers the DNA(s) to a cell. For example, recombinant AAV (rAAV) vectors can be used to deliver DNA encoding miDNM1s. Other vectors (for example, other viral vectors such as lentivirus, adenovirus, retrovirus, equine-associated virus, alphavirus, pox viruses, herpes virus, polio virus, sindbis virus and vaccinia viruses) can also be used to deliver polynucleotides encoding miDNM1s. Thus, also provided are viral vectors encoding one or more miDNM1s. When the viral vector is a rAAV, the rAAV lack AAV rep and cap genes. The rAAV can be self-complementary (sc) AAV. As another example, non-viral vectors such as lipid nanoparticles can be used for delivery.

Provided herein are rAAV, each encoding a miDNM1. Also provided are rAAV encoding one or more miDNM1s. A rAAV (with a single-stranded genome, scAAV) encoding one or more miDNM1s can encode one, two, three, four, five, six, seven or eight miDNM1s. A scAAV encoding one or more miDNM1s can encode one, two, three or four miDNM1s.

Compositions are provided comprising the nucleic acids or viral vectors described herein.

Further provided are methods of preventing or inhibiting expression of the DNM1 gene in a cell comprising contacting the cell with a delivery vehicle (such as rAAV) encoding a miDNM1 wherein, if the delivery vehicle is rAAV, the rAAV lacks rep and cap genes. In the methods, expression of the duplicated and/or mutant DNM1 allele is inhibited by at least 10, at least 20, at least 30, at least 40, at least 50, at least 60, at least 70, at least 80, at least 90, at least 95, at least 98 percent, at least 99 percent, or 100 percent. In the methods, expression of the wild-type DNM1 allele is inhibited by at least 10, at least 20, at least 30, at least 40, at least 50, at least 60, at least 70, at least 80, at least 90, at least 95, at least 98 percent, at least 99 percent, or 100 percent.

Still further provided are methods of delivering DNA encoding a miDNM1 to an subject in need thereof, comprising administering to the subject a delivery vehicle (such as rAAV) comprising DNA encoding the miDNM1 wherein, if the delivery vehicle is rAAV, the rAAV lacks rep and cap genes. Other methods of delivering DNA encoding the miDNM1 to an subject in need thereof, comprise administering to the subject a delivery vehicle (such as rAAV) comprising DNA encoding one or more miDNM1 wherein, if the delivery vehicle is rAAV, the rAAV lacks rep and cap genes.

Methods are also provided of preventing or treating DEE comprising administering a delivery vehicle (such as rAAV) comprising DNA encoding a miDNM1 wherein, if the delivery vehicle is rAAV, the rAAV lacks rep and cap genes. Other methods of preventing or treating DEE comprise administering a delivery vehicle (such as rAAV) comprising DNA encoding one or more miDNM1 wherein, if the delivery vehicle is rAAV, the rAAV lacks rep and cap genes. The methods result in restoration of DNM1 expression to at least 25 percent, at least 30, at least 40, at least 50, at least 60, at least 70, at least 80, at least 90, at least 95, at least 98 percent, at least 99 percent, or 100 percent or more, of normal DNM1 expression in an unaffected subject.

The disclosure provides a delivery vehicle that is a viral vector comprising the nucleic acids described herein and/or a combination of any one or more thereof. Viral vectors provided include, but are not limited to an adeno-associated virus (AAV), adenovirus, lentivirus, retrovirus, poxvirus, baculovirus, herpes simplex virus, vaccinia virus, or a synthetic virus. The viral vector can be an AAV. The AAV lacks rep and cap genes. The AAV can be a recombinant AAV (rAAV) or a self-complementary recombinant AAV (scAAV). The AAV is, for example, AAV-1, AAV-2, AAV-3, AAV-4, AAV-5, AAV-6, AAV-7, AAV-8, AAV-9, AAV-10, AAV-11, AAV-12, AAV-13, AAV-anc80, or AAV rh.74. The AAV can be AAV-9. The AAV can be a pseudotyped AAV, for example, an AAV2/8 or AAV2/9.

The disclosure provides a composition comprising the nucleic acids described herein and a pharmaceutically acceptable carrier. The disclosure provides a composition comprising a viral vector comprising the nucleic acids described herein, and/or a combination of any one or more thereof and a pharmaceutically acceptable carrier.

The disclosure provides a composition comprising a delivery vehicle capable of delivering to cells a nucleic acid encoding a miDNM1, wherein the miDNM1 binds a segment of a mRNA encoded by a human DNM1 gene (wherein the segment either does or does not encode sequence comprising a mutation associated with DEE); wherein the segment is conserved relative to the wild-type mouse DNM1 gene, and, optionally, a pharmaceutically acceptable carrier. The human DNM1 gene exon 10a can comprise the sequence of SEQ ID NO: 52, or a variant thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99%, identity. The mouse DNM1 gene exon 10a can comprise the sequence of SEQ ID NO: 54, or a variant thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99%, identity. A miDNM1 specifically binds, for example, a mRNA segment that is complementary to a sequence within nucleotides 115-136 of SEQ ID NO: 52 (the nucleotides bound by, for example, miDNM1a-4). The human DNM1 gene exon 10b can comprise the sequence of SEQ ID NO: 53, or a variant thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99%, identity. The mouse DNM1 gene exon 10b can comprise the sequence of SEQ ID NO: 55, or a variant thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99%, identity.

The disclosure provides a delivery vehicle in the compositions that is a viral vector. The viral vector in the compositions can be, for example, an adeno-associated virus (AAV), adenovirus, lentivirus, retrovirus, poxvirus, baculovirus, herpes simplex virus, vaccinia virus, or a synthetic virus. The viral vector can be an AAV. The AAV lacks rep and cap genes. The AAV can be a recombinant AAV (rAAV) or a self-complementary recombinant AAV (scAAV). The AAV is or has a capsid serotype selected from, for example, AAV-1, AAV-2, AAV-3, AAV-4, AAV-5, AAV-6, AAV-7, AAV-8, AAV-9, AAV-10, AAV-11, AAV-12, AAV-13, AAV-anc80, and AAV rh.74. The AAV can be or can have a capsid serotype of AAV-9. The AAV can be a pseudotyped AAV, such as AAV2/8 or AAV2/9.

The disclosure provides methods of delivering to a neuron comprising a duplicated and/or mutant DNM1 gene: (a) a nucleic acid comprising a template nucleic acid encoding a miDNM1 comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the polynucleotide sequence set forth in any one of SEQ ID NOs: 1-17; a nucleic acid encoding the full length miDNM1 sequences set out in any one of SEQ ID NOs: 9-16 or variants thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% identity to the sequence set forth in any one of SEQ ID NOs: 18-34; or a nucleic acid encoding a miDNM1 processed antisense guide strand comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the polynucleotide sequence set forth in any one of SEQ ID NOs: 35-51; (b) a vector comprising any one or more of the nucleic acids described herein; or (c) a composition comprising any one or more of the nucleic acids or vectors described herein.

The disclosure provides a method of treating a subject suffering from a duplicated and/or mutant DNM1 gene, the method comprising administering to the subject (a) a nucleic acid comprising a template nucleic acid encoding a miDNM1 comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the polynucleotide sequence set forth in any one of SEQ ID NOs: 1-17; a nucleic acid encoding the full length miDNM1 sequences set out in any one of SEQ ID NOs: 9-16 or variants thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% identity to the sequence set forth in any one of SEQ ID NOs: 18-34; or a nucleic acid encoding a miDNM1 processed antisense guide strand comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the polynucleotide sequence set forth in any one of SEQ ID NOs: 35-51; (b) a vector comprising any one or more of the nucleic acids described herein; or (c) a composition comprising any one or more of the nucleic acids or vectors described herein.

The disclosure contemplates the subject treated by methods herein suffers from DEE. The disclosure also contemplates treatment of a subject that is at risk for DEE due to a mutation of the DNM1 gene. The subject can be a mammalian animal. The subject can be a human subject.

The disclosure also provides uses of at least one nucleic acid as described herein, at least one viral vector as described herein, or a composition as described herein in making a medicament for, or in treating a subject suffering from, a pathogenic DNM1 gene variant.

The disclosure also provides uses of at least one nucleic acid as described herein, at least one viral vector as described herein, or a composition as described herein in making a medicament for or in treating DEE in a subject in need thereof.

Other features and advantages of the disclosure will be apparent from the following description of the drawing and the detailed description. It should be understood, however, that the drawing, detailed description, and the examples, while indicating embodiments of the disclosed subject matter, are given by way of illustration only, because various changes and modifications within the spirit and scope of the disclosure will become apparent from the drawing, detailed description, and the examples.

BRIEF DESCRIPTION OF THE DRAWINGS

This patent or application file contains at least one drawing executed in color. Copies of this patent or patent application publication with color drawing(s) will be provided by the United States Patent and Trademark Office upon request and payment of the necessary fee.

FIG. 4A-C shows miDnm1a improves survival in a dose dependent manner (C57BL/6J strain background pilot experiment; related to FIG. 2A-C). A) Experimental plan for pilot studies. Three miDnm1a doses were administered to neonates and examined for survival and growth. B) The survival curve for treated Dnm1$^{Ftfl/Ftfl}$ mice is significantly different from untreated Dnm1$^{Ftfl/Ftfl}$ mice only for the 1.85×10$^{11}$ (n=10) and 3.2×10$^{11}$ (n=6) doses (p=0.0001, p=0.01, respectively, log-rank Mantel-Cox test). C) For these doses, treated Dmn1$^{Ftfl/Ftfl}$ mice show growth improvement compared to untreated mice (p=0.003, repeated measures ANOVA).

FIG. 5A-F shows scAAV9-miDnm1a treatment improves developmental outcomes. A) Treatment significantly improved the grip strength at PND 11 of Dnm1$^{Ftfl/Ftfl}$ mice (n=30) compared to control-injected (n=28) mice (p=0.0009, least squares regression using rank- and normal-quantile transformed data), with no effect of litter size, sex or virus dose. Treated Dmn1$^{Ftfl/Ftfl}$ mice did not differ from treated (n=24) or control-injected (n=19) Dnm1$^{+/+}$ mice (same test as above with Tukey's HSD post-hoc test, p>0.05). B,C) In an assay for sensorimotor development, at PND 9 and PND 11, control-injected Dnm1$^{Ftfl/Ftfl}$ mice had a higher latency, albeit not significant for the easier 90° turn (p>0.05, least squares regression using rank- and normal-quantile transformed data, Dunnett's post-hoc test). However, for the more difficult 180° turn, control-injected Dnm1$^{Ftfl/Ftfl}$ mice showed a significantly higher latency at PND 11 compared to the other 3 groups (p<0.001, Dunnet's post-hoc test). D) Control-injected Dnm1$^{Ftfl/Ftfl}$ mice (n=24) show severe ataxia, importantly, treatment with miDnm1a (n=17) eliminates this phenotype (p=6.9×10$^{-17}$, log-Poisson test) and restores Dnm1$^{Ftfl/Ftfl}$ motor coordination back to the level of treated (n=16) and control-injected (n=23) Dnm1$^{+/+}$ mice (p=0.19 mixed model log-Poisson test). E,F) Using locomotion and velocity as a proxy for possible hyperactivity, we observed that there was no significant difference between all groups (p>0.05, one-way ANOVA).

STATISTICAL ANALYSIS RELATING TO THE FIGURES

Figure 1:
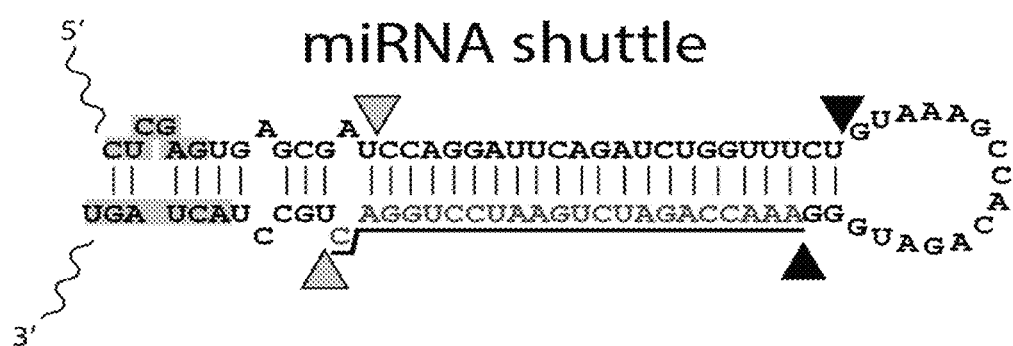
FIG. 1 shows an example of an artificial miRNA shuttle sequence to demonstrate folding and processing sites. The mature guide strand is underlined. Grey arrowheads indicate Drosha cut sites; black arrowheads indicate Dicer cut sites. Shaded sequences at extreme 5' and 3' ends are restriction sites in the template DNA used to clone the miRNA shuttles in front of the U6 promoter.

Statistical analysis was done using either Prism 8 software (GraphPad, Inc), JMP 14 software (JMP, Inc), depending on the test. qPCR data (FIG. 2) were analyzed using 2-way ANOVA (Prism 8). Survival analysis for the pilot study (FIG. 3) was analyzed using the log-rank Mantel-Cox test (Prism 8), and for the primary study (FIG. 4) the Proportional Hazards test with risk ratios was used to accommodate covariates (JMP 14). Growth (FIG. 3, FIG. 4) was analyzed using repeated measures MANOVA (JMP). Seizure-like behaviors (FIG. 3) were analyzed using 2×2 Fisher Exact Test (JMP 14). Grip strength and negative geotaxis (FIG. 5) were analyzed using least squares regression after rank- and normal-quantile transformation of the data (JMP). Ataxia (counts of falls and wobbles) was analyzed using the log-Poisson test and contrast modeling to compare specific groups (JMP 14). IHC quantifications were analyzed using Poisson overdispersion option in the Generalized Analysis for Linear Models module (gamlj) in Jamovi.[31] P-values were Bonferroni adjusted.

DETAILED DESCRIPTION

The products and methods described herein are used in the treatment of diseases associated with a pathogenic DNM1 isoform. Diseases associated with DNM1 include, for example, DEEs. DEEs include, but are not limited to, Lennox-Gastout Syndrome and Infantile Spasms.

At least twenty heterozygous de novo variants identified in thirty-three patients predominantly in the critical GTPase and the middle domains of the DNM1 are described in EuroEPINOMICS-RES Consortium, Am. J. Hum. Genet., 100: 179 (2017); Asinof (2015), supra; von Spiczak, supra; Brereton et al., Mol. Genet. Genomic Med., 6: 294-300

(2018); Kolnikova et al., Seizure, 56: 31-33 (2018); and Li et al., Front. Pharmacol., 10: 1454, (2019).

A nucleic acid encoding human DNM1 exon 10a is set forth in SEQ ID NO: 52. A nucleic acid encoding human DNM1 exon 10b is set forth in SEQ ID NO: 53. Various products and methods of the disclosure can target variants of the human DNM1 nucleotide sequence set forth in SEQ ID NO: 52 or 53. The variants can exhibit 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, and 70% identity to the nucleotide sequence set forth in SEQ ID NO: 52 or 53.

A nucleic acid encoding mouse DNM1 exon 10a is set forth in SEQ ID NO: 54. A nucleic acid encoding mouse DNM1 exon 10b is set forth in SEQ ID NO: 54. Various products and methods of the disclosure can target variants of the nucleotide sequence set forth in SEQ ID NO: 54 or 55. The variants can exhibit 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, and 70% identity to the nucleotide sequence set forth in SEQ ID NO: 54 or 55.

The disclosure includes the use of RNA interference to inhibit or interfere with the expression of DNM1 to ameliorate and/or treat subjects with diseases or disorders resulting from overexpression of DNM1. RNA interference (RNAi) is a mechanism of gene regulation in eukaryotic cells that has been considered for the treatment of various diseases. RNAi refers to post-transcriptional control of gene expression mediated by inhibitory RNAs. The inhibitory RNAs are small (21-25 nucleotides in length), noncoding RNAs that share sequence homology and base-pair with cognate messenger RNAs (mRNAs). The interaction between the inhibitory RNAs and mRNAs directs cellular gene silencing machinery to prevent the translation of the mRNAs. The RNAi pathway is summarized in Duan (Ed.), Section 7.3 of Chapter 7 in Muscle Gene Therapy, Springer Science+Business Media, LLC (2010).

As an understanding of natural RNAi pathways has developed, researchers have designed artificial inhibitory RNAs for use in regulating expression of target genes for treating disease. Several classes of small RNAs are known to trigger RNAi processes in mammalian cells [Davidson et al., *Nat. Rev. Genet.*, 12:329-40 (2011); Harper, *Arch. Neurol.*, 66:933-938 (2009)]. Artificial inhibitory RNAs expressed in vivo from plasmid- or virus-based vectors and may achieve long term gene silencing with a single administration, for as long as the vector is present within target cell nuclei and the driving promoter is active [Davidson et al., *Methods Enzymol.*, 392:145-73, (2005)]. Importantly, this vector-expressed approach leverages the decades-long advancements already made in the muscle gene therapy field, but instead of expressing protein coding genes, the vector cargo in RNAi therapy strategies are artificial inhibitory RNAs targeting disease genes-of-interest.

An shRNA is an artificial RNA molecule with a tight hairpin turn that can be used to silence target gene expression via RNA interference (RNAi). shRNA is an advantageous mediator of RNAi in that it has a relatively low rate of degradation and turnover, but it requires use of an expression vector. Once the vector has transduced the host genome, the shRNA is then transcribed in the nucleus by polymerase II or polymerase III, depending on the promoter choice. The product mimics pri-microRNA (pri-miRNA) and is processed by Drosha. The resulting pre-shRNA is exported from the nucleus by Exportin 5. This product is then processed by Dicer and loaded into the RNA-induced silencing complex (RISC). The sense (passenger) strand is degraded. The antisense (guide) strand directs RISC to mRNA that has a complementary sequence. In the case of perfect complementarity, RISC cleaves the mRNA. In the case of imperfect complementarity, RISC represses translation of the mRNA. In both of these cases, the shRNA leads to target gene silencing.

The disclosure includes the production and administration of viral vectors expressing artificial DMN1 inhibitory RNAs. The expression of the artificial DMN1 inhibitory RNAs is regulated by the use of various promoters. The disclosure contemplates use of polymerase III promoters, such as U6 and H1 promoters, or polymerase II promoters.

The products and methods provided herein can comprise miRNA shuttles to modify DNM1 expression (e.g., knockdown or inhibit expression). Like shRNAs, miRNA shuttles are expressed intracellularly from DNA transgenes. miRNA shuttles typically contain natural miRNA sequences required to direct correct processing, but the natural, mature miRNA duplex in the stem is replaced by the sequences specific for the intended target transcript (e.g., as shown in FIG. 1). Following expression, the artificial miRNA is cleaved by Drosha and Dicer to release the embedded siRNA-like region. Polymerase III promoters, such as U6 and H1 promoters, and polymerase II promoters are also used to drive expression of the miRNA shuttles.

The disclosure provides sequences encoding miDNM1s to inhibit the expression of the DNM1 gene. The disclosure provides a nucleic acid encoding a miDNM1 comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the full length miDNM! polynucleotide sequence set forth in any one of SEQ ID NOs: 18-34. The disclosure provides a nucleic acid encoding a miDNM1 processed antisense guide strand comprising at least about 70%, 75, 80%, 81%, 82%, 83%, 84%, 85%, 86%, 87%, 88%, 89%, 90%, 91%, 92%, 93%, 94%, 95%, 96%, 97%, 98%, 99%, or 100% identity to the antisense guide strand polynucleotide sequence set forth in any one of SEQ ID NOs: 35-51.

The disclosure provides a nucleic acid encoding a miDNM1 comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the polynucleotide sequence set forth in any one of SEQ ID NOs: 1-17.

Exemplary miDNM1s comprise the polynucleotide sequence set out in any one or more of SEQ ID NOs: 18-34, or a variant thereof comprising at least about 70%, 75%, 80%, 81%, 82%, 83%, 84%, 85%, 86%, 87%, 88%, 89%, 90%, 91%, 92%, 93%, 94%, 95%, 96%, 97%, 98%, or 99% identity to any one of SEQ ID NOs 18-34. Final processed guide strand sequences corresponding to SEQ ID NOs: 18-34 are respectively set out in SEQ ID NOs: 35-51. The disclosure additionally provides the antisense guide strands set out in SEQ ID NOs: 35-51 and contemplates variants of each of those antisense guide strands that are at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% identical.

The disclosure contemplates polynucleotides encoding one or more copies of these sequences are combined into a single delivery vehicle, such as a vector. Thus, the disclosure includes vectors comprising a nucleic acid of the disclosure or a combination of nucleic acids of the disclosure. Provided are viral vectors (such as adeno-associated virus (AAV), adenovirus, retrovirus, lentivirus, equine-associated virus, alphavirus, pox virus, herpes virus, herpes simplex virus, polio virus, sindbis virus, vaccinia virus or a synthetic virus, e.g., a chimeric virus, mosaic virus, or pseudotyped virus, and/or a virus that contains a foreign protein, synthetic polymer, nanoparticle, or small molecule) to deliver the nucleic acids disclosed herein. AAV vectors are exemplified.

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_001862; at least portions of AAV-7 and AAV-8 genomes are provided in GenBank Accession Nos. AX753246 and AX753249, respectively; the AAV-9 genome is provided in Gao et al., *J. Virol.*, 78: 6381-6388 (2004); the AAV-10 genome is provided in *Mol. Ther.*, 13(1): 67-76 (2006); the AAV-11 genome is provided in *Virology*, 330(2): 375-383 (2004); portions of the AAV-12 genome are provided in Genbank Accession No. DQ813647; portions of the AAV-13 genome are provided in Genbank Accession No. EU285562. The sequence of the AAV rh.74 genome is provided in see U.S. Pat. No. 9,434,928, incorporated herein by reference. The sequence of the AAV-B1 genome is provided in Choudhury et al., *Mol. Ther.*, 24(7): 1247-1257 (2016). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56 to 65° C. for several hours), making cold preservation of AAV less critical. AAV may even be lyophilized. Finally, AAV-infected cells are not resistant to superinfection.

As exemplified herein, the AAV vector lacks rep and cap genes. The AAV can be a recombinant AAV (rAAV) or a self-complementary recombinant AAV (scAAV). The AAV has a capsid serotype can be from, for example, AAV-1, AAV-2, AAV-3, AAV-4, AAV-5, AAV-6, AAV-7, AAV-8, AAV-9, AAV-10, AAV-11, AAV-12, AAV-13, AAV-anc80, AAV rh.74, AAV rh.8, or AAVrh.10.

Viral vectors provided include, for example, AAV1 (i.e., an AAV containing AAV1 inverted terminal repeats (ITRs) and AAV1 capsid proteins), AAV2 (i.e., an AAV containing AAV2 ITRs and AAV2 capsid proteins), AAV3 (i.e., an AAV containing AAV3 ITRs and AAV3 capsid proteins), AAV4 (i.e., an AAV containing AAV4 ITRs and AAV4 capsid proteins), AAV5 (i.e., an AAV containing AAV5 ITRs and AAV5 capsid proteins), AAV6 (i.e., an AAV containing AAV6 ITRs and AAV6 capsid proteins), AAV7 (i.e., an AAV containing AAV7 ITRs and AAV7 capsid proteins), AAV8 (i.e., an AAV containing AAV8 ITRs and AAV8 capsid proteins), AAV9 (i.e., an AAV containing AAV9 ITRs and AAV9 capsid proteins), AAVrh74 (i.e., an AAV containing AAVrh74 ITRs and AAVrh74 capsid proteins), AAVrh.8 (i.e., an AAV containing AAVrh.8 ITRs and AAVrh.8 capsid proteins), AAVrh.10 (i.e., an AAV containing AAVrh.10 ITRs and AAVrh.10 capsid proteins), AAV11 (i.e., an AAV containing AAV11 ITRs and AAV11 capsid proteins), AAV12 (i.e., an AAV containing AAV12 ITRs and AAV12 capsid proteins), or AAV13 (i.e., an AAV containing AAV13 ITRs and AAV13 capsid proteins).

DNA plasmids of the disclosure comprise recombinant AAV (rAAV) genomes of the disclosure. The DNA plasmids are transferred to cells permissible for infection with a helper virus of AAV (e.g., adenovirus, E1-deleted adenovirus or herpes virus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV-anc80, and AAV rh.74. IAAV DNA in the rAAV genomes can be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13, AAV-anc80, and AAV rh.74. Other types of rAAV variants, for example rAAV with capsid mutations, are also included in the disclosure. See, for example, Marsic et al., Molecular Therapy 22(11): 1900-1909 (2014). As noted above, the nucleotide sequences of the genomes of various AAV serotypes are known in the art. Use of cognate components is specifically contemplated. Production of pseudotyped rAAV is disclosed in, for example, WO 01/83692 which is incorporated by reference herein in its entirety.

The AAV vector can be a pseudotyped AAV, containing ITRs from one AAV serotype and capsid proteins from a different AAV serotype. The pseudo-typed AAV can be AAV2/9 (i.e., an AAV containing AAV2 ITRs and AAV9 capsid proteins). The pseudotyped AAV can be AAV2/8 (i.e., an AAV containing AAV2 ITRs and AAV8 capsid proteins). The pseudotyped AAV can be AAV2/1 (i.e., an AAV containing AAV2 ITRs and AAV1 capsid proteins).

The AAV vector can contain a recombinant capsid protein, such as a capsid protein containing a chimera of one or more of capsid proteins from AAV1, AAV2, AAV3, AAV4, AAV5, AAV6, AAV7, AAV8, AAV9, AAVrh74, AAVrh.8, or AAVrh.10, AAV10, AAV11, AAV12, or AAV13. Other types of rAAV variants, for example rAAV with capsid mutations, are also contemplated. See, for example, Marsic et al., Molecular Therapy, 22(11): 1900-1909 (2014). As noted above, the nucleotide sequences of the genomes of various AAV serotypes are known in the art.

The disclosure provides AAV to deliver miDNM1s which target DNM1 mRNA to inhibit DNM1 expression. AAV can be used to deliver miDNM1s under the control of an RNA polymerase III (Pol III)-based promoter. AAV is used to deliver miDNM1s under the control of a U6 promoter. AAV is used to deliver miDNM1s under the control of a H1 promoter. AAV is used to deliver miDNM1s under the control of an RNA polymerase II (Pol II)-based promoter. AAV is used to deliver miDNM1s under the control of an U7 promoter. AAV is used to deliver miDNM1s under the control of a neuron-specific promoter. For example, AAV is used to deliver miDNM1s under the control of a neuron-specific synapsin promoter. AAV is used to deliver miDNM1s under the control of a DNM1 promoter.

In nature, the U6 promoter controls expression of the U6 RNA, a small nuclear RNA (snRNA) involved in splicing, and which has been well-characterized [Kunkel et al., Nature, 322(6074):73-77 (1986); Kunkel et al., Genes Dev. 2(2):196-204 (1988); Paule et al., Nuc. Acids Res., 28(6): 1283-1298 (2000)]. The U6 promoter is used to control vector-based expression in mammalian cells [Paddison et al., Proc. Natl. Acad. Sci. USA, 99(3):1443-1448 (2002); Paul et al., Nat. Biotechnol., 20(5):505-518 (2002)] because (1) the promoter is recognized by RNA polymerase III (poly III) and controls high-level, constitutive expression of RNA; and (2) the promoter is active in most mammalian cell types. The disclosure includes use of both murine and human U6 promoters.

AAV vectors herein lack rep and cap genes. The AAV can be a recombinant AAV, a recombinant single-stranded AAV (ssAAV), or a recombinant self-complementary AAV (scAAV).

rAAV genomes of the disclosure comprise one or more AAV ITRs flanking a polynucleotide encoding, for example, one or more miDNM1s. Commercial providers such as Ambion Inc. (Austin, TX), Darmacon Inc. (Lafayette, CO), InvivoGen (San Diego, CA), and Molecular Research Laboratories, LLC (Herndon, VA) generate custom inhibitory RNA molecules. In addition, commercial kits are available to produce custom siRNA molecules, such as SILENCER™ siRNA Construction Kit (Ambion Inc., Austin, TX) or psiRNA System (InvivoGen, San Diego, CA).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing [Samulski et al., Proc. Natl. Acad. S6. USA, 79:2077-2081 (1982)], addition of synthetic linkers containing restriction endonuclease cleavage sites [Laughlin et al., Gene, 23:65-73 (1983)] or by direct, blunt-end ligation [Senapathy & Carter, J. Biol. Chem., 259:4661-4666 (1984)]. The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, Current Opinions in Biotechnology, 1533-1539 (1992); and Muzyczka, Curr. Topics in Microbiol. and Immunol., 158: 97-129 (1992). Various approaches are described in Ratschin et al., Mol. Cell. Biol. 4:2072 (1984); Hermonat et al., Proc. Natl. Acad. Sci. USA, 81: 6466 (1984); Tratschin et al., Mol. Cell. Biol. 5: 3251 (1985); McLaughlin et al., J. Virol., 62: 1963 (1988); and Lebkowski et al., Mol. Cell. Biol., 7: 349 (1988). Samulski et al., J. Virol., 63: 3822-3828 (1989); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al., Vaccine, 13:1244-1250 (1995); Paul et al., Hum. Gene Ther., 4:609-615 (1993); Clark et al., Gene Ther., 3: 1124-1132 (1996); U.S. Pat. Nos. 5,786,211; 5,871,982; 6,258,595; and McCarty, Mol. Ther., 16(10): 1648-1656 (2008). The foregoing documents are hereby incorporated by reference in their entirety herein, with particular emphasis on those sections of the documents relating to rAAV production. The production and use of self-complementary (sc) rAAV are specifically contemplated and exemplified.

The disclosure further provides packaging cells that produce AAV vectors. Packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

Recombinant AAV (rAAV) (i.e., infectious encapsidated rAAV particles) are thus provided herein. The genomes of the rAAV lack AAV rep and cap DNA, that is, there is no AAV rep or cap DNA between the ITRs of the genomes of the rAAV.

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69: 427-443 (2002); U.S. Pat. No. 6,566,118 and WO 98/09657.

Compositions comprising the nucleic acids and viral vectors of the disclosure are provided. Compositions comprising delivery vehicles (such as rAAV) described herein are provided. Such compositions also comprise a pharmaceutically acceptable carrier. The compositions may also comprise other ingredients such as diluents and adjuvants. Acceptable carriers, diluents and adjuvants are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

For CSF delivery including but not limited to intrathecal delivery, compositions provided herein can comprise a pharmaceutically acceptable aqueous excipient containing a non-ionic, low-osmolar compound or contrast agent such as iobitridol, iohexol, iomeprol, iopamidol, iopentol, iopromide, ioversol, or ioxilan, where the aqueous excipient containing the non-ionic, low-osmolar compound can have one or more of the following characteristics: about 180 mgI/mL, an osmolality by vapor-pressure osmometry of about 322 mOsm/kg water, an osmolarity of about 273 mOsm/L, an absolute viscosity of about 2.3 cp at 20° C. and about 1.5 cp at 37° C., and a specific gravity of about 1.164 at 37° C. Exemplary compositions comprise about 20 to 40% non-ionic, low-osmolar compound or about 25% to about 35% non-ionic, low-osmolar compound. An exemplary composition comprises scAAV or rAAV viral particles formulated in 20 mM Tris (pH8.0), 1 mM $MgCl_2$, 200 mM NaCl, 0.001% poloxamer 188 and about 25% to about 35% non-ionic, low-osmolar compound. Another exemplary composition comprises scAAV formulated in and 1× PBS and 0.001% Pluronic F68.

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$, about $1 \times 10^{14}$, about $1 \times 10^{16}$, or more DNase resistant particles (DRP) per ml. Dosages may be expressed in units of viral genomes (vg). Dosages contemplated herein include about $1 \times 10^7$ vg, about $1 \times 10^5$ vg, about $1 \times 10^9$ vg, about $5 \times 10^9$ vg, about $6 \times 10^9$ vg, about $7 \times 10^9$ vg, about $8 \times 10^9$ vg, about $9 \times 10^9$ vg, about $1 \times 10^{10}$ vg, about $2 \times 10^{10}$ vg, about $3 \times 10^{10}$ vg, about $4 \times 10^{10}$ vg, about $5 \times 10^{10}$ vg, about $1 \times 10^{11}$ vg, about $1.1 \times 10^{11}$ vg, about $1.2 \times 10^{11}$ vg, about $1.3 \times 10^{11}$ vg, about $1.2 \times 10^{11}$ vg, about $1.3 \times 10^{11}$ vg, about $1.4 \times 10^{11}$ vg, about $1.5 \times 10^{11}$ vg, about $1.6 \times 10^{11}$ vg, about $1.7 \times 10^{11}$ vg, about $1.8 \times 10^{11}$ vg, about $1.9 \times 10^{11}$ vg, about $2 \times 10^{11}$ vg, about $3 \times 10^{11}$ vg, about $4 \times 10^{11}$ vg, about $5 \times 10^{11}$ vg, about $1 \times 10^{12}$ vg, about $1 \times 10^{13}$ vg, about $1.1 \times 10^{13}$ vg, about $1.2 \times 10^{13}$ vg, about $1.3 \times 10^{13}$ vg, about $1.5 \times 10^{13}$ vg, about $2 \times 10^{13}$ vg, about $2.5 \times 10^{13}$ vg, about $3 \times 10^{13}$ vg, about $3.5 \times 10^{13}$ vg, about $4 \times 10^{13}$ vg, about $4.5 \times 10^{13}$ vg, about $5 \times 10^{13}$ vg, about $6 \times 10^{13}$ vg, about $1 \times 10^{14}$ vg, about $2 \times 10^{14}$ vg, about $3 \times 10^{14}$ vg, about $4 \times 10^{14}$ vg, about $5 \times 10^{14}$ vg, about $1 \times 10^{15}$ vg, to about $1 \times 10^{16}$ vg, or more total viral genomes. Dosages of about $1 \times 10^9$ vg to about $1 \times 10^{10}$ vg, about $5 \times 10^9$ vg to about $5 \times 10^{10}$ vg, about $1 \times 10^{10}$ vg to about $1 \times 10^{11}$ vg, about $1 \times 10^{11}$ vg to about $1 \times 10^{15}$ vg, about $1 \times 10^{12}$ vg to about $1 \times 10^{15}$ vg, about $1 \times 10^{12}$ vg to about $1 \times 10^{14}$ vg, about $1 \times 10^{13}$ vg to about $6 \times 10^{14}$ vg, and about $6 \times 10^{13}$ vg to about $1.0 \times 10^{14}$ vg, $2.0 \times 10^{14}$ vg, $3.0 \times 10^{14}$ vg, $5.0 \times 10^{14}$ are also contemplated. For example, CSF doses can range between about $1 \times 10^{13}$ vg/patient to about $1 \times 10^{15}$ vg/patient based on age groups. For example, intravenous delivery doses can range between $1 \times 10^{13}$ vg/kilogram (kg) body weight and $2 \times 10^{14}$ vg/kg.

Methods of transducing a target cell with a delivery vehicle (such as rAAV), in vivo or in vitro, are contemplated. The in vivo methods comprise the step of administering an effective dose, or effective multiple doses, of a composition comprising a delivery vehicle (such as rAAV) to an subject (including a human patient) in need thereof. If the dose is administered prior to development of a disorder/disease, the administration is prophylactic. If the dose is administered after the development of a disorder/disease, the administration is therapeutic. An effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the invention is a DEE. DEE include, but are not limited to, Lennox-Gastaut Syndrome and Infantile Spasms. In families known to carry pathological DNM1 gene variants, the methods can be carried out before the onset of disease. In other patients, the methods are carried out after diagnosis.

For intrathecal administration, the subject can be held in the Trendelenburg position (head down position) after injection of the rAAV (e.g., for about 5, about 10, about 15 or about 20 minutes). For example, the patient may be tilted in the head down position at about 1 degree to about 30 degrees, about 15 to about 30 degrees, 30 to about 60 degrees, about 60 to about 90 degrees, or about 90 to about 180 degrees.

Molecular, biochemical, histological, and functional outcome measures demonstrate the therapeutic efficacy of the methods. Outcome measures are described, for example, in Aimiuwu et al., *Mol. Ther.*, 28(7): 1706-1716 (2020). Outcome measures include, but are not limited to, one or more of the reduction or elimination of mutant DNM1 mRNA or protein in affected tissues, DNM1 gene knockdown, increased survival, increased growth, and decreased seizures. Others include, but are not limited to, improved nerve histology (axon number, axon size and myelination), improved motor function, improved grip strength, reduction in gliosis and neurodegeneration in the brain, and improved metabolic activity.

In the methods of the disclosure, expression of variant DNM1 in a subject is inhibited by at least 10, at least 20, at least 30, at least 40, at least 50, at least 60, at least 70, at least 80, at least 90, at least 95, at least 98 percent, at least 99 percent, or 100 percent compared to expression in the subject before treatment.

Combination therapies are also contemplated by the invention. Combination as used herein includes both simultaneous treatment and sequential treatments. Combinations of methods described herein with standard medical treatments and supportive care are specifically contemplated.

Administration of an effective dose of a nucleic acid, viral vector, or composition of the disclosure may be by routes standard in the art including, but not limited to, intramuscular, parenteral, intravascular, intravenous, oral, buccal, nasal, pulmonary, intracranial, intracerebroventricular, intrathecal, intraosseous, intraocular, rectal, or vaginal. An effective dose can be delivered by a combination of routes. For example, an effective dose is delivered intravenously and intramuscularly, or intravenously and intracerebroventricularly, and the like. An effective dose can be delivered in sequence or sequentially. An effective dose can be delivered simultaneously. Route(s) of administration and serotype(s) of AAV components of the rAAV (in particular, the AAV ITRs and capsid protein) of the invention are chosen and/or matched by those skilled in the art taking into account the infection and/or disease state being treated and the target cells/tissue(s) that are to express the miRNAs.

In particular, actual administration of delivery vehicle (such as rAAV) may be accomplished by using any physical method that will transport the delivery vehicle (such as rAAV) into a target cell of an subject. Administration includes, but is not limited to, injection into muscle, the bloodstream and/or directly into the nervous system or liver. Simply resuspending a rAAV in phosphate buffered saline has been demonstrated to be sufficient to provide a vehicle useful for muscle tissue expression, and there are no known restrictions on the carriers or other components that can be co-administered with the rAAV (although compositions that degrade DNA should be avoided in the normal manner with rAAV). Capsid proteins of a rAAV may be modified so that the rAAV is targeted to a particular target tissue of interest such as neurons. See, for example, WO 02/053703, the disclosure of which is incorporated by reference herein. Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The delivery vehicle (such as rAAV) can be used with any pharmaceutically acceptable carrier for ease of administration and handling.

A dispersion of delivery vehicle (such as rAAV) can also be prepared in glycerol, sorbitol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol, sorbitol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

Transduction of cells such as neurons with rAAV provided herein results in sustained expression of DNM1 miRNAs. The present invention thus provides methods of administering/delivering rAAV which express DNM1 miRNAs to a subject, preferably a human being. These methods include transducing cells and tissues (including, but not limited to, central nervous system neurons) with one or more rAAV described herein. Transduction may be carried out with gene cassettes comprising cell-specific control elements.

The term "transduction" is used to refer to, as an example, the administration/delivery of miDNM1s to a target cell either in vivo or in vitro, via a replication-deficient rAAV described herein resulting in the expression of miDNM1s by the target cell (e.g., neurons).

Thus, methods are provided of administering an effective dose (or doses, administered essentially simultaneously or doses given at intervals) of rAAV described herein to subject in need thereof.

EXAMPLES

Aspects and exemplary embodiments of the invention are illustrated by the following examples.

Example 1

Design and In Vitro Testing of miDNM1 Targeting Murine DNM1

To knock down Dnm1$^{Ftfl}$, microRNAs were designed that specifically and efficiently target the murine Dnm1a isoform that harbors the fitful mutation.

Artificial miRNAs are based on the natural mir-30, maintaining important structural and sequence elements required for normal miRNA biogenesis but replacing the mature mir-30 sequences with 22-nt of complementarity with the DNM1 gene. See FIG. 1 which shows an exemplary general miRNA shuttle structure.

Four microRNAs targeting Dnm1a (termed miDnm1a-1 through miDnm1a-4) were designed and cloned into a mir-30 based construct with expression driven by the U6 promoter, as previously described in Wallace et al., *Mol. Ther. J. Am. Soc. Gene Ther.*, 20: 1417-1423 (2012). The miDNM1 sequences were generally designed according to Boudreau et al., Chapter 2 of Harper (Ed.), RNA Interference Techniques, Neuromethods, Vol. 58, Springer Science+Business Media, LLC (2011). Qualifying miRNAs were 22 nt long, with the first four and last four nucleotides being at least 75% GC rich and AU rich respectively. Additionally, the string of 22 nucleotides were 40% AU rich. miRNA specific targeting of Dnm1a capitalized on the 42 nt difference between Dnm1a and Dnm1b.

The activity of the miRNAs was tested in vitro using a dual luciferase reporter assay. The luciferase assay requires development of a dual reporter plasmid containing 2 different luciferase genes from firefly and *Renilla reniformis*, respectively. DNM1 gene sequences are inserted as the 3' UTR of *Renilla* luciferase, while firefly luciferase serves as an internal control. U6.miDNM1 plasmids are co-transfected into HEK293 cells with the dual luciferase plasmid. DNM1 gene knockdown is determined by measuring activity of *Renilla* luciferase tagged with DNM1 sequences, relative to the control firefly luciferase activity. miDnm1a-1 exhibited about 84% knockdown, while miDnm1a-2 exhibited about 64% knockdown and miDnm1a-3 exhibited about 80% knockdown. miDnm1a-4 was the most effective at reducing the amount of Dnm1a mRNA (FIG. 2A), exhibiting about 95% knockdown. The full length miDnm1a-4 miRNA sequence is as follows.

(SEQ ID NO: 19)
5' CUCGAGUGAGCGAACCAUCAGAAAGUGUAGUGAACUGUAAAGCCAC

AGAUGGGUUCACUACACUUUCUGAUGGUGUGCCUACUAGA 3'

The antisense strand of the mature miRNA (underlined) binds Dnm1a mRNA.

Example 2

Production of scAAV9 Encoding miDNM1s

Figure 2A:
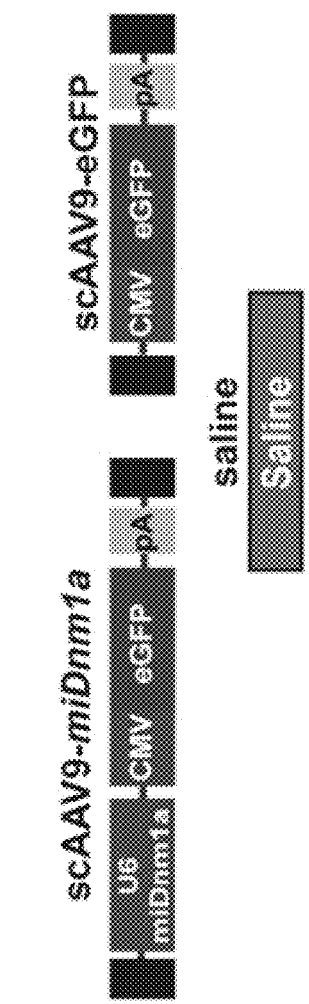
FIG. 2A-D shows scAAV9-miDnm1a selectively inhibits Dnm1a. A) Knockdown efficacy of Dnm1a in vitro by 4 different miRNA constructs. miDnm1a-4 was the most effective with 95% knockdown. B) Experimental and control constructs delivered via ICV injection at PND 0. The black boxes indicate the viral inverted terminal repeats, and pA indicates an SV40 polyadenylation signal. C) Validation of Dnm1a knockdown efficacy in vivo by scAAV9-miDnm1a (n=8) compared to scAAV9-eGFP control (n=6) shows significant decrease of Dnm1a but not Dnm1b in whole brain extracts from scAAV9-miDnm1a treated mice ($p<0.0001$; ns, respectively; 2-way ANOVA with Sidak's correction for multiple comparisons). D) Broad viral transduction of both Dnm1$^{Ftfl/Ftfl}$ and Dnm1$^{+/+}$ scAAV9-miDnm1a treated mice 30 days after ICV injection. Images were taken at 10× magnification. Data reported as mean±SEM. Scale bar on whole brain represents 500 μm, and scale bar of region of interest (ROI) represents 20 μm.
Figure 2B:
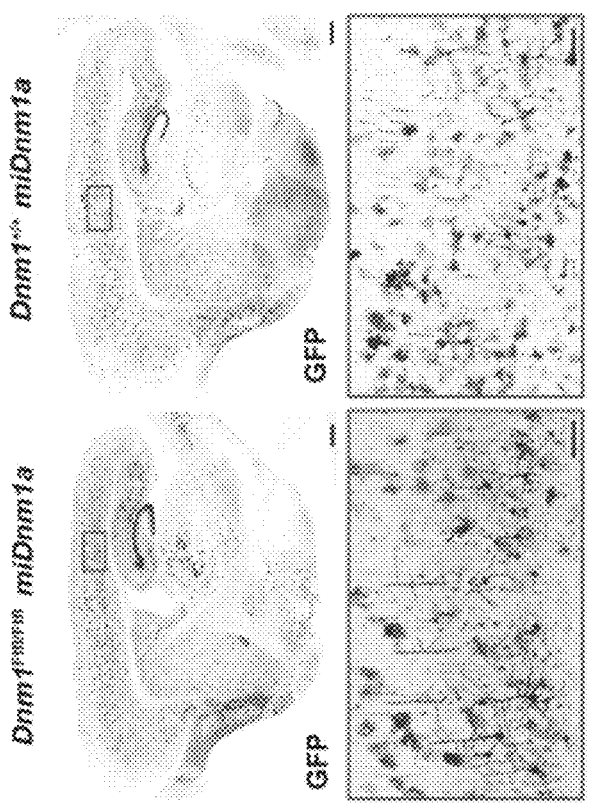

Next, miDnm1a-4 template DNA was cloned into a scAAV9 virus vector (scAAV9-miDnm1a) for in vivo validation (FIG. 2B).

The miDNM1 template sequences were cloned into the scAAV9 construct generically named "scAAV9-NP vectors" for in vivo delivery. The scAAV9 also contained a CMV promoter-driven eGFP reporter gene. The scAAV9 comprised a mutant AAV2 inverted terminal repeat (ITR) and a wild type AAV2 ITR that enable packaging of self-complementary AAV genomes. The resulting scAAV9 are referred to as "scAAV9-NP vectors". A non-targeting scAAV referred to as "AAV9-miRLacZ" (short for a scAAV construct scAAV-NP.U6.miRLacZ.CMV.eGFP).

The scAAV9 were produced by transient transfection procedures using a double-stranded AAV2-ITR-based vector, with a plasmid encoding Rep2Cap9 sequence as previously described [Gao et al., *J. Virol.*, 78: 6381-6388 (2004)] along with an adenoviral helper plasmid pHelper (Stratagene, Santa Clara, CA) in 293 cells. The scAAV9 were produced in three separate batches for the experiments and purified by two cesium chloride density gradient purification steps, dialyzed against PBS and formulated with 0.001% Pluronic-F68 to prevent virus aggregation and stored at 4° C. All vector preparations were titered by quantitative PCR using Taq-Man technology. Purity of vectors was assessed by 4-12% sodium dodecyl sulfate-acrylamide gel electrophoresis and silver staining (Invitrogen, Carlsbad, CA). scAAV9 viruses were generated and titered by the Viral Vector Core at The Research Institute at Nationwide Children's Hospital.

Example 3

In Vivo Quantification of Transduction and Dnm1a Knockdown

Mice were either administered the treatment (scAAV9-miDnm1a) or control (scAAV9-eGFP) AAV via a one-time bilateral intracerebroventricular (ICV) injection at postnatal day zero (PND 0).

For ICV delivery of scAAV9-miDnm1a, PND 0 Dnm1$^{+/+}$ mice were anesthetized using hypothermia by being placed on a chilled metal block until properly anesthetized. The injection site was approximately $2/5^{th}$ the distance from the lambda suture to each eye. All injections were executed free hand using a point style 4, 33-gauge needle and a 104 or 254 Hamilton syringe (Cat #65460-06 and Cat #65460-10). Control scAAV9-eGFP injections were matched to miDnm1a dosage, and saline controls were matched to the volume of virus injected.

Whole brain was isolated from six eGFP and eight miDnm1a injected mice at PND 14. The tissues were flash frozen with 2-Methylbutane and stored at −80° C. Samples were homogenized using a dounce and RNA was isolated using TRIzol Reagent (ThermoFisher, Waltham, MA, Cat #15596018). RNA was converted to cDNA using Invitrogen SuperScript III First-Strand Synthesis System (Carlsbad, CA, Cat #18080051). Dnm1a knock down was assessed using the primers 5'-CTCGCTTTTGAAGCCACAGT-3' (SEQ ID NO: 56) and 3'-TTTCTGATGGTGGACGTGAG-5' (SEQ ID NO: 57). Dnm1b expression was evaluated using the primers 5'-GGCCTTTGAAACCATTGTGA-3' (SEQ ID NO: 58), and 3'-GCACTGTCTAACCGTGCTGA-5' (SEQ ID NO: 59). SYBR™ Select Master Mix (Applied Biosystems, Waltham, MA, Cat #4472903) was used for qPCR which was run using Applied Biosystems-Quant Studio 5.

Figure 2C:
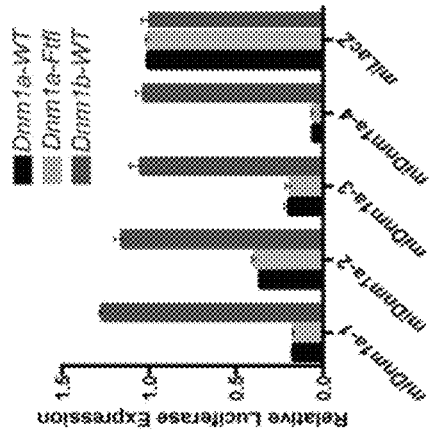
Figure 2D:
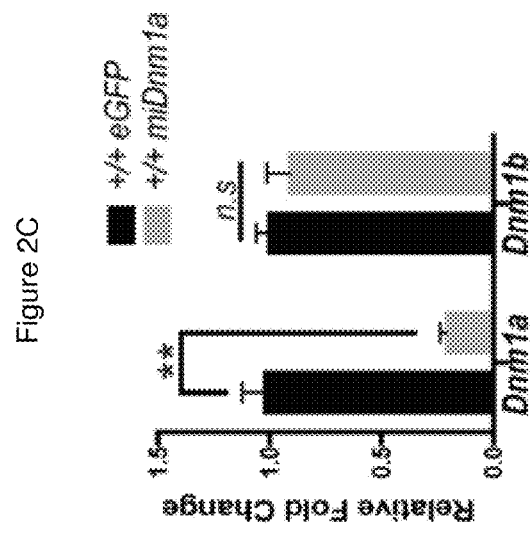

Results are shown in FIG. 2C-D.

Example 4

Pilot Study

To assess the efficacy of scAAV9-miDnm1a in extending survival, a pilot study was conducted in the C57BL/6J (B6J) mouse strain background. Dnm1$^{Ftfl/Ftfl}$ mice experience severe and fully-penetrant tonic-clonic seizures and comorbidities resulting in lethality by the third postnatal week, irrespective of mouse strain background.[11] B6J-Dnm1$^{Ftfl/Ftfl}$ mice were treated with three doses of miDnm1a: $1×10^{10}$, $1.85×10^{11}$, $3.25×10^{11}$ vector genomes (vg).

Treatment of Dnm1$^{Ftfl/Ftfl}$ mutants extended survival in a dose-dependent manner: 30% (p=0.0001) and 50% (p=0.01) of mice treated with the latter two doses respectively, survived to PND 30 and showed growth improvements (p=0.003; FIGS. 4B-C). The highest dose at $3.25×10^{11}$ vg did not produce overt adverse effects.

Example 5

Expanded Study

Figure 3A:
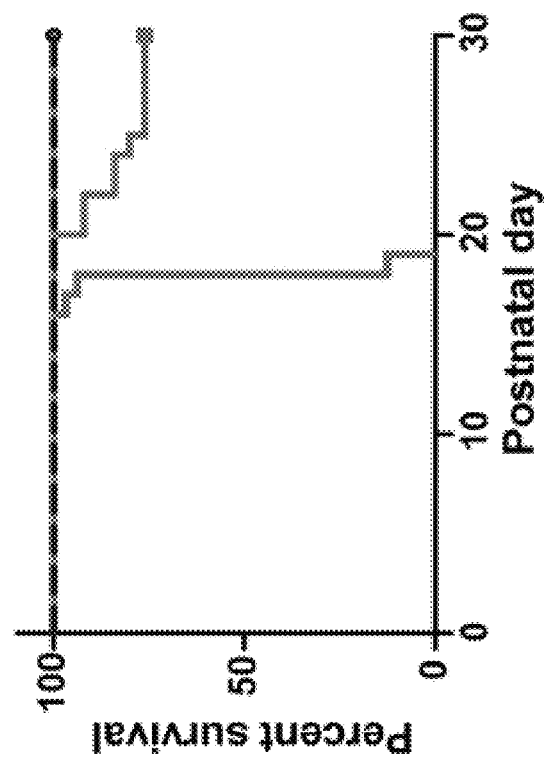
FIG. 3A-D shows scAAV9-miDnm1a treatment of C57BL/6J mice improves survival, growth and seizure outcomes. A) Experimental design with ICV injection administered at PND 0, developmental phenotyping executed between PND 4-PND 11, survival, seizure and growth measurement assessed from PND 4-PND 30 (the endpoint of the study) and cellular phenotyping performed at PND 18 and PND 30. B) Treatment with miDnm1a led to 75% survival of Dnm1$^{Ftfl/Ftfl}$ mice (n=25) to PND 30 compared to control-injected mice (eGFP or saline, n=27) which were 100% lethal before PND 20 ($p<0.0001$, log-rank Mantel-Cox test). Treated Dnm1$^{Ftfl/Ftfl}$ mice differed from treated Dnm1$^{+/+}$ (n=24) or control-injected Dnm1$^{+/+}$ (n=19) mice (p=0.0239; p=0.0097, respectively; log-rank Mantel-Cox test). C) Although treated and control-injected Dnm1$^{Ftfl/Ftfl}$ mice were notably smaller as early as PND 8, miDnm1a treated Dnm1$^{Ftfl/Ftfl}$ showed growth improvement beginning at PND 12. Repeated measures ANOVA was performed until PND 18 when control-injected Dmn1$^{Ftfl/Ftfl}$ mice exited the study, including genotype-treatment effects (combining the two control treatments, eGFP and saline), plus other independent variables including sex, virus dose and litter size. For treated vs. control-injected Dnm1$^{Ftfl/Ftfl}$, the effect of treatment was highly significant (p=3.3×10$^{-13}$), despite a significant effect of litter size (p=1.4×10$^{-7}$) but no significant impact of virus dose or sex. Growth differences at the PND 30 study endpoint between treated Dnm1$^{Ftfl/Ftfl}$ and treated wildtype were significant (p=0.004), with a modest effect of litter size (p=0.048). Using similar analysis, treated wildtype mice also showed growth delay compared to control wildtype (p=0.004), with a modest effect of sex (p=0.01) and litter size (p=0.033). D) Both miDnm1a treated and control-injected Dnm1$^{Ftfl/Ftfl}$ mice show seizure-like behavior, however, control-injected Dnm1$^{Ftfl/Ftfl}$ mice had significantly more seizures at PND 14 and PND 18. Seizure-behaviors of treated mice decreased over time. See Table 1 for sample numbers and analysis. Data reported as mean±SEM. See also FIG. 4A-C.

To further evaluate the effectiveness of miDnm1a, (B6J× FVB/NJ)F$_2$ hybrid background mice were used because of their large litter size, animal size and good maternal care. Dnm1$^{Ftfl/Ftfl}$ and Dnm1$^{+/+}$ F$_2$ hybrids were either treated (scAAV9-miDnm1a) or control-injected (i.e., scAAV9-eGFP or saline; FIG. 3A) at PND 0. F2 mice were treated with $5.2×10^{11}$ vg to $6.0×10^{11}$ vg per mouse based on the titers acquired. Mice were observed for survival, seizure activity and weight until PND 30, the chosen endpoint for this study (FIG. 3A).

Study Design

Experiments were performed blinded to genotype and treatment, and randomized as appropriate. Postnatal day (PND) 30 was selected prospectively as the adult endpoint because pups are typically weaned between PND 22 and PND 28, marking the end of the developmental period. To conform with institutional compliance data collection from live $Dnm1^{Ftfl/Ftfl}$ mice was stopped upon moribundity. For 95% confidence in detecting improvement from inhibition of mutant Dnm1a, at least 12 animals per group (genotype x treatment, sexes combined) was necessary to detect an effect with 80% power. For the primary study, to assess a possible dose effect two experiments were executed in the F2 hybrid background, representing two viral doses: $5.2 \times 10^{11}$ vg; $6.0 \times 10^{11}$ vg. Mice were randomly assigned to either miDnm1a treatment or control condition which included eGFP or saline administration; in analysis for simplicity the two control conditions were combined since they did not differ in effect. Thus, for analysis when modeling treated vs. control-injected groups we combined as covariates the two dose-experiments and sexes (using categorical indicator variables for each) and litter size. Cellular analysis was executed at PND 18, because that is the timepoint by which almost all untreated or control-injected mice become moribund, and PND 30, the endpoint of the study. For this study, we show three representative replicates for the cellular characterization of the effect of miDnm1a treatment.

Animals and Genotyping

C57BL/6J-$Dnm1^{Ftfl-flox}$ mice used for these studies (hereafter termed B6J-$Dnm1^{Ftfl}$) were generated in $Dnm1^{\Delta 1a/\Delta 1a}$ mice by The Jackson Laboratory's Genetic Engineering Technology core, introducing the $Dnm1^{Ftfl}$ mutation using CRISPR/Cas9. To generate interstrain F2 hybrid mice, B6J-$Dnm1^{Ftfl/+}$ mice were mated to FVB/NJ females (JAX, Bar Harbor, ME, stock 004624), and F1 hybrid mice mated inter se. Mice were genotyped with a PCR protocol designed to detect the presence of loxP sites in the fitful allele. The genotyping primers 5'-CCTCTCTGTCCACTTGTAGC-CATT-3' (SEQ ID NO: 60) and 3'-ACTGGGTGATGCT-CACTAGAACCT-5' (SEQ ID NO: 61) produce a 321 bp mutant allele and a 215 bp wildtype allele. Mice for this study were between 0 and 30 days old. To identify individual pups, they were tattooed at PND 0 according to the AIMS pup tattoo identification system (Budd Lake, NJ) using Ketchum Animal Tattoo Ink (Cat #329AA). Mice were also ear notched at PND 10. Post weaning at PND 21, mice had access to food and water in their home cages ad libitum. Pups were never separated from their home cage for more than 10 mins at a time. Lights were maintained on a 12 h light/dark cycle with behavioral testing occurring during the light portion of the cycle. All procedures were approved by Columbia University's Institutional Animal Care and Use Committee and were performed in accordance with the National Institute of Health Guide for the care and use of laboratory animals.

Example 6

Evaluation of Growth, Development and Seizures in Treated Mice

Growth and Survival Monitoring

Between PND 4 and PND 30, Example 5 mice were weighed every other day. In addition, general health and survival were monitored every day from PND 0 to PND 30 (study endpoint).

Figure 3B:
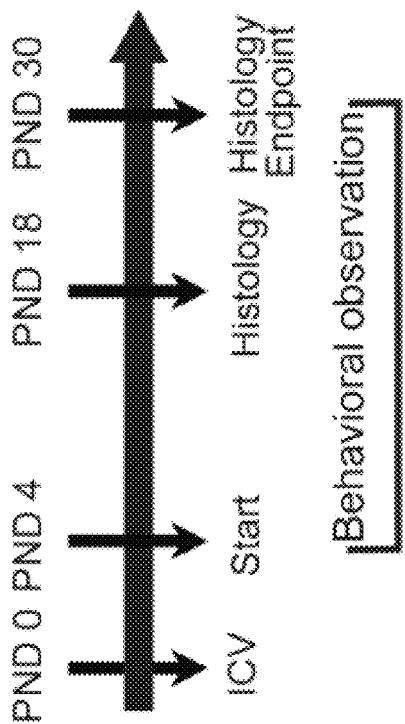
Figure 3C:
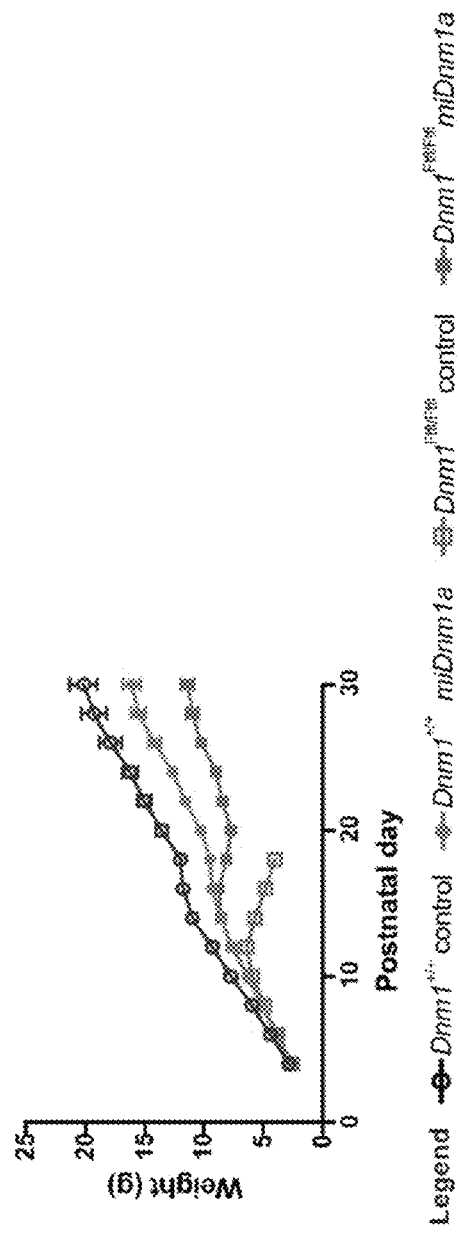

As shown from prior studies [Boumil, supra], control-injected $Dnm1^{Ftfl/Ftfl}$ mice started showing growth deficits from PND 8 until moribundity or a terminal seizure event by PND 18-19 (FIG. 3B, C). In contrast, treated $Dnm1^{Ftfl/Ftfl}$ mice grew steadily until PND 30, although they lagged behind treated and control-injected $Dnm1^{+/+}$ mice starting at PND 8 and PND 18, respectively (FIG. 3C). Overall, there was a significant growth improvement in treated $Dnm1^{Ftfl/Ftfl}$ mice compared to control-injected $Dnm1^{Ftfl/Ftfl}$ by PND 18 (repeated measures ANOVA; $p=3.3 \times 10^{-13}$). Even treated $Dnm1^{+/+}$ mice showed some growth delay starting at PND 8 compared to control-injected $Dnm1^{+/+}$ ($p=0.004$; FIG. 3C). Although germline Dnm1a null mice were previously reported to lack any overt impairments [Asinof (2015), supra; Asinof (2015), supra], it is plausible that modest growth delay as seen in treated $Dnm1^{+/+}$ is a feature of postnatal Dnm1a elimination. Alternatively, the growth deficits observed in treated $Dnm1^{+/+}$ mice could be due to unpredictable off-target effects of miDnm1a. Regardless, these data reinforce the effectiveness of miDnm1a in improving growth outcomes of $Dnm1^{Ftfl/Ftfl}$ mice.

Seizure Quantification

To determine the effect of miDnm1a on seizure phenotypes, treated and control-injected $Dnm1^{Ftfl/Ftfl}$ homozygotes were assessed for overt seizure and seizure-associated activity. Each litter of pups were monitored for approximately 5 mins during weighing. Seizure activity was characterized by wild runs, Straub tail, vertical jumps that lasted more than 10 sec with subsequent facial grooming, continuous jerking of the forelimbs and hindlimbs and tonic-clonic seizures. All seizures within the observation window were counted as one event. The assessments were done on alternate days, starting at PND 14 during weight examination sessions.

TABLE 1

Observed seizure or seizure associated behaviors in treated or control-injected $Dnm1^{Ftfl/Ftfl}$ mice

| Postnatal day | Group | Positive | Negative | total | % positive | p-value[a] |
|---|---|---|---|---|---|---|
| 14 | Control | 25 | 19 | 44 | 56.8% | 0.017 |
|  | miDnm1a | 8 | 21 | 29 | 27.6% |  |
| 16 | Control | 24 | 19 | 43 | 55.8% | 0.156 |
|  | miDnm1a | 11 | 18 | 29 | 37.9% |  |
| 18 | Control | 39 | 3 | 42 | 92.9% | $2 \times 10^{-6}$ |
|  | miDnm1a | 12 | 17 | 29 | 41.4% |  |
| 20 | miDnm1a | 5 | 19 | 24 | 20.8% | n.a. |
| 22 | miDnm1a | 9 | 12 | 21 | 20.8% | n.a. |
| 24 | miDnm1a | 7 | 13 | 20 | 35.0% | n.a. |

TABLE 1-continued

Observed seizure or seizure associated behaviors
in treated or control-injected Dnm1$^{Ftfl/Ftfl}$ mice

| Postnatal day | Group | Positive | Negative | total | % positive | p-value[a] |
|---|---|---|---|---|---|---|
| 26 | miDnm1a | 3 | 17 | 20 | 15.0% | n.a. |
| 28 | miDnm1a | 1 | 19 | 20 | 5.0% | n.a. |
| 30 | miDnm1a | 1 | 19 | 20 | 5.0% | n.a. |

[a]Fisher exact test, 2-tail, 2 × 2 contingency analysis.

Figure 3D:
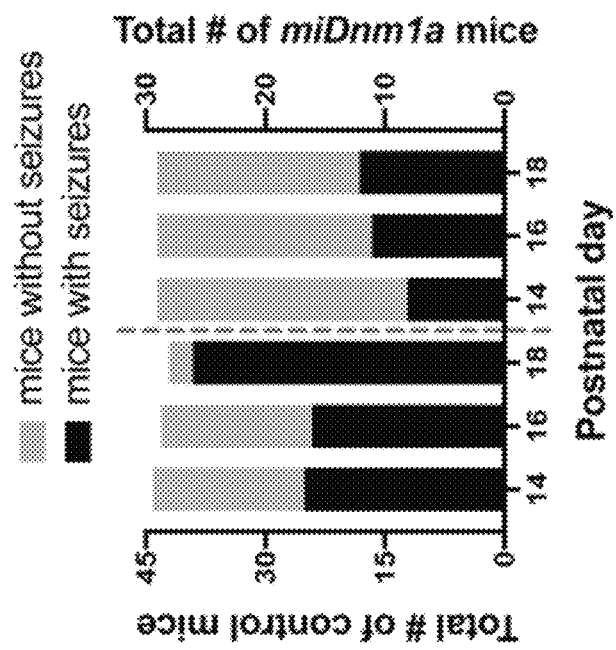

While both treated and control-injected Dnm1$^{Ftfl/Ftfl}$ mice exhibited seizure behaviors, treated mice had fewer overall observed events between PND 14-18 (FIG. 3D, Table 1). By PND 18, all control-injected Dnm1$^{Ftfl/Ftfl}$ mice were moribund and incapable of staying upright. Treated Dnm1$^{Ftfl/Ftfl}$ mice showed handling seizures between PND 14-24 (Table 1). After this period, the number and intensity of their observed seizure and seizure-like events decreased (FIG. 3D, Table 1). These data suggest that miDnm1a treatment decreased seizures and seizure-associated activity in Dnm1$^{Ftfl/Ftfl}$ mice.

Development

Developmental milestones in pups are important readouts of developmental delays. To begin the test, each pup was gently removed from the nest and placed on a clean piece of bench protector. The cage lid was immediately and gently placed back, to reduce agitation in the nest. All assessment was completed by a deft experimenter within 3 min. At the end of the session, the pup was quickly returned to the nest. For all behaviors, mice from both groups (genotype x treatment) were handled every day from PND 4-12. On all even days (PND 4 to PND 12) they were weighed and on odd days (PND 5 to PND 11), they were assessed for strength and sensorimotor development. From PND 14 to PND 30 mice were weighed on every other day on even days. Testing was executed blind.

Vertical Screen Hold

To evaluate strength, mice were placed on a vertical mesh screen and their latency to fall off the screen was recorded. Mice were observed for 30 sec and were allowed two attempts to complete the task. The scores from both trials were averaged. Mice were tested at PND 9 and PND 11 because the average age of a rodent to perform this task is PND 8.

Treated Dnm1$^{Ftfl/Ftfl}$ mice (n=30) showed improved grip strength compared to control-injected Dnm1$^{Ftfl/Ftfl}$ mice (n=28) at PND 11 (p=0.0009; FIG. 5A). However, treated Dnm1$^{Ftfl/Ftfl}$ mice did not differ in grip strength from treated (n=24) or control-injected (n=19) Dnm1$^{+/+}$ at PND 9 and PND 11 (p>0.05; FIG. 5A).

Negative Geotaxis

Possible sensorimotor impairment was evaluated using the negative geotaxis assay, which challenges the innate behavior in mice to utilize vestibular cues for motor coordination. Mice are placed head down on a mesh screen set at a 45° angle. The latency for the pups to turn 90° (sideways) and 180° (heads up) from a downward facing start position was recorded. Mice were given 30 sec to perform the task and were allowed two attempts. Both attempts were averaged for the analysis.

Unlike control-injected Dnm1$^{Ftfl/Ftfl}$ mice, treated Dnm1$^{Ftfl/Ftfl}$ mice like wildtype controls, tended to exhibit a shorter latency to turn 90° and 180° at PND 11, but only the more challenging 180° turn was statistically significant compared with control-injected Dnm1$^{Ftfl/Ftfl}$ mice (p=0.0004; FIG. 5B, C).

Open Field

To quantify the ataxic phenotype, we observed PND 14 pups in the open field using the EthoVision XT video tracking software (Noldus). Mice were tested in a 28.5 cm arena with luminescence of 100 lux. Mice were recorded for 10 minutes. Videos were subsequently scored blind by counting the number of times each mouse wobbled or fell during movement over a 10-min window. Mice that moved less than 100 cm were excluded. Additionally, distance travelled and velocity of each mouse was quantified.

As expected, control-injected Dnm1$^{Ftfl/Ftfl}$ mice had numerous ataxic events (overtly wobbly gait and falls), but miDnm1a treatment completely abolished this ataxic phenotype observed in the control-injected Dnm1$^{Ftfl/Ftfl}$ mice (p<0.0001; FIG. 5D). Ambulation was also quantitated during this time and no difference was found in either distance traveled or velocity between groups (p>0.05; FIG. 5E, F).

These results show that miDnm1a treatment improved the developmental outcomes of Dnm1$^{Ftfl/Ftfl}$ mice.

Summary

Treated Dnm1$^{Ftfl/Ftfl}$ mice showed extended survival, improved growth, decreased lethal seizures, improved developmental outcomes, and an absence of ataxia. These data together show the effectiveness of miDnm1a at curbing or eliminating the most severe fitful behavioral phenotypes including seizures, growth and ataxia, culminating in an overall improvement in their quality of life and survival to the endpoint.

Example 7

Histology

The significant mitigating effect of Dnm1$^{Ftfl}$ mRNA silencing on severe seizures and impaired neurodevelopment prompted examination of the extent to which treatment impacts underlying cellular pathology. Gliosis and neuronal cell death are hallmarks of neuronal insults and recurrent seizure activity, features not previously examined in the published studies on Dnm1$^{Ftfl}$ mouse model. Here the presence of gliosis and cell degeneration was investigated via immunolabeling using glial fibrillary acidic protein (GFAP) and Fluoro-Jade C (FJC).

At least 3-5 mice from each group (genotype: Dnm1$^{Ftfl/Ftfl}$ and Dnm1$^{+/+}$ X treatment: miDnm1a and eGFP) were perfused with 4% PFA for immunohistochemical assessment at PND 18. We also evaluated Dnm1$^{Ftfl/Ftfl}$ miDnm1a mice surviving until PND 30 and Dnm1$^{+/+}$ controls. All animals were handled in the same way prior to euthanasia. Brains were dissected from the skull and postfixed in 4% PFA overnight at 4° C. Brains were transferred to gradient concentrations of sucrose (15% and 30%) overnight at 4° C. Once saturated, the brains were embedded in OCT (Fisher Healthcare Cat #4585) and frozen. Free floating 40 μm sections were collected using a cryostat (Leica CM3050S). The sections were permeabilized with 0.1% Triton X in PBS for 30 minutes and blocked with 5% normal goat serum in PBS (blocking buffer) for 1 h at room temperature. Slices were incubated with either anti-NPY (1:500, ImmunoStar, Hudson, WI Cat #22940), anti-c-Fos (1:250, Abcam, Cambridge, UK, Cat #ab190289), anti-GFP (1:250, Invitrogen, Carlsbad, CA, Cat #A11120) or anti-GFAP (1:750, Sigma, Saint Louis, MO, Cat. #M4403) in blocking buffer overnight at 4° C. Afterwards, sections were washed in PBST for 10 min and incubated in AlexaFluor secondary 555 (1:1000, Thermo Fisher Scientific, Waltham, MA, Ref #A31428 and Ref #A32727) for 2 h at room temperature. Sections were incubated in DAPI for 5 mins before washing with PBS. Sections were finally mounted on slides and cover slipped with Fluoromount-G (Southern Biotech, Birmingham, AL, Cat #0100-01).

For FJC labeling, 3-5 PND 18 and PND 30 mice (genotype x treatment) were euthanized, and their brains dissected and flash frozen. 20 μm thick sections were collected with a cryostat and mounted on gelatin coated slides (FD Neuro-Technologies, Inc. Columbia, MD, Cat #P0101). Sections were post fixed with 2% PFA and washed in PBS. Slides were air dried on a 50° C. heating block for 20-30 mins and subsequently placed in 80% ethanol solution consisting of 1% NAOH for 5 mins. Slides were moved to 70% ethanol for 2 mins, rinsed in deionized water for 2 mins, incubated in 0.06% potassium permanganate in deionized water for 10 mins, rinsed for 2 mins in deionized water, and finally incubated in FJC working solution consisting of 0.0001% FJC in 0.1% acetic acid for 10 mins. Finally, slides were washed 3 times for 2 mins each in deionized water, air dried completely and cleared in xylene for at least 1 min before they were cover slipped with mounting media (DPX, Saint Louis, MO, Cat #06522).[30] Slides were imaged using a Zeiss LSM-800 confocal microscope and Zen v2.3. Tiled images of 10× magnification were acquired of the hippocampus for each section keeping the laser and gain settings constant. For FJC, the Axio X-Cite series 120 Q epifluorescence microscope was used and images of 10× magnification were acquired. Post processing of images was carried out with Adobe Photoshop. All image processing was kept consistent.

IHC images were quantified blind using ImageJ (Fiji; nih.gov). Images were converted to 8-bit and brightness and contrast keep constant. The cell counter plugin was used to count aberrant NPY and c-Fos positive cells in the whole hippocampal CA3 and to count FJC positive cells in the hippocampal CA1. GFAP fluorescence intensity was determined using the measure tool with the region of interest (ROI) in the CA1. Measurements were set to include area, min and max gray value and integrated density. For fluorescence intensity measurement, background intensity was collected. Relative fluorescence was calculated by first subtracting the integrated intensity of the background from the integrated intensity of the CA1 ROI to yield a background corrected intensity. Area was kept constant across all intensity measures. The corrected intensities of the wildtype control group was then averaged. Each corrected intensity was divided by the average of the wildtype control corrected intensity and multiplied by 100.

Figure 6A:
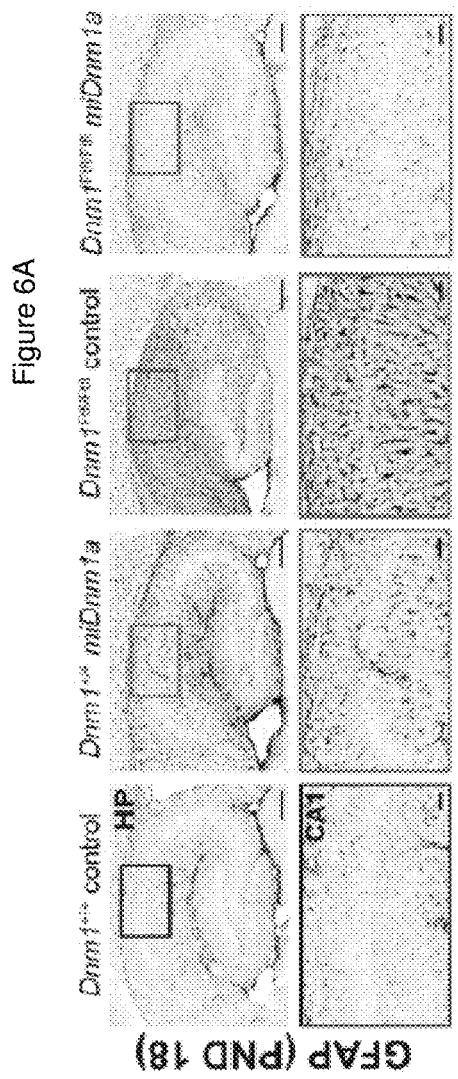
FIG. 6A-D shows miDnm1a treatment diminishes gliosis and cellular degeneration at PND 18 until PND 30. A) Control-injected Dnm1$^{Ftfl/Ftfl}$ mice showed strikingly increased gliosis specifically in the hippocampal CA1 as identified with the marker GFAP compared to treated Dnm1$^{Ftfl/Ftfl}$ mice (p=0.018). Treated Dnm1$^{Ftfl/Ftfl}$ mice did not differ from treated and control-injected Dnm1$^{+/+}$ mice (p>0.05) at PND 18. B) By PND 30, treated Dnm1$^{Ftfl/Ftfl}$ showed significantly more GFAP intensity compared to treated and control-injected Dnm1$^{+/+}$ mice (p=0.0052 and p=0.0072 respectively). Images (A-B) were taken at 10× magnification and analysis was done using an Ordinary one-way ANOVA followed by Tukey's multiple comparisons test. Scale bar of entire hippocampus represents 200 μm and region of interest (ROI) scale bar represents 20 μm. C, D) FJC labeling at PND 18 showed significant cell death in the hippocampus of control-injected Dnm1$^{Ftfl/Ftfl}$ mice, specifically along the CA1, unlike treated Dnm1$^{Ftfl/Ftfl}$ mice (p=0.015). Treated Dnm1$^{Ftfl/Ftfl}$ mice did not differ from treated and control-injected Dnm1$^{+/+}$ mice (p>0.05). By PND 30, treated Dnm1$^{Ftfl/Ftfl}$ mice had little apparent cell death as identified by FJC labeling. However, they did not differ from treated and control-injected Dnm1$^{+/+}$ mice (p>0.05). Images were taken at 10× magnification and scale bars correspond to 100 μm. Analyses were executed using the Poisson overdispersion option in the GMLJ module of Jamovi's software. 3-5 mice were used in these analysis and data are reported as mean±SEM. See also FIG. 7A-B.
Figure 6B:
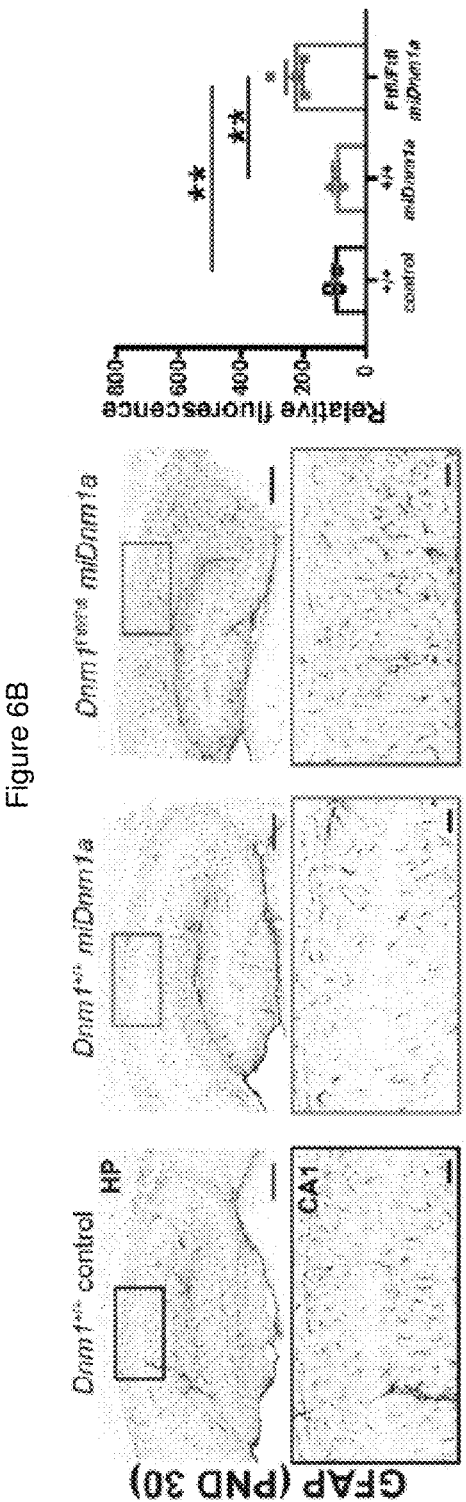
Figure 6C:
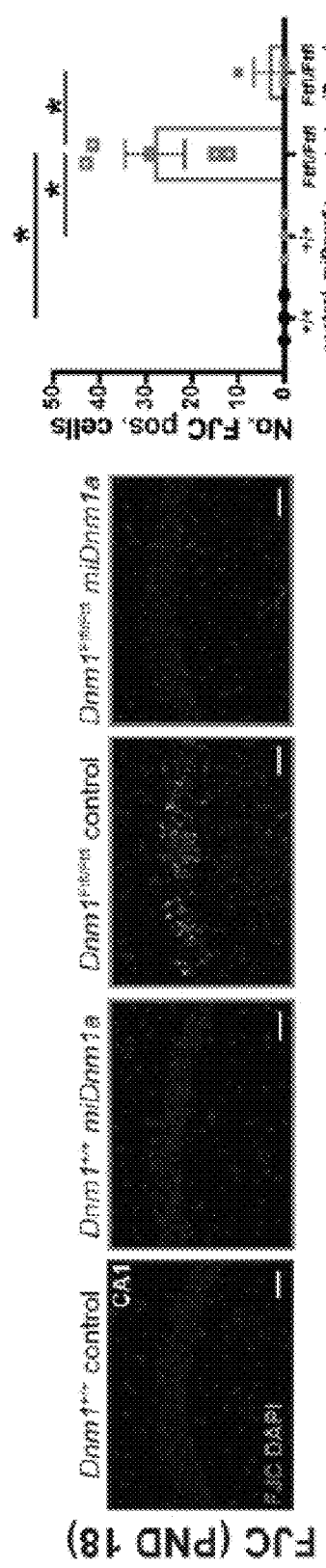
Figure 6D:
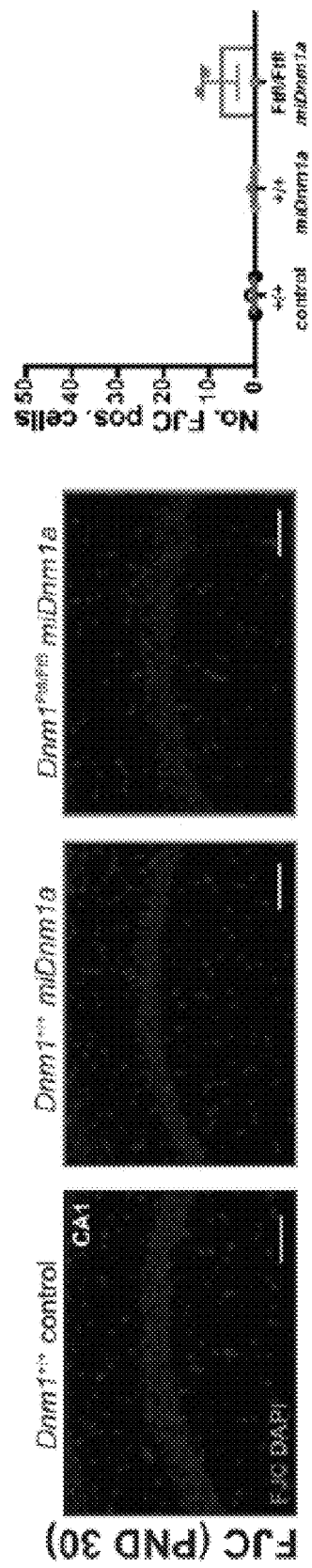
Figure 7A:
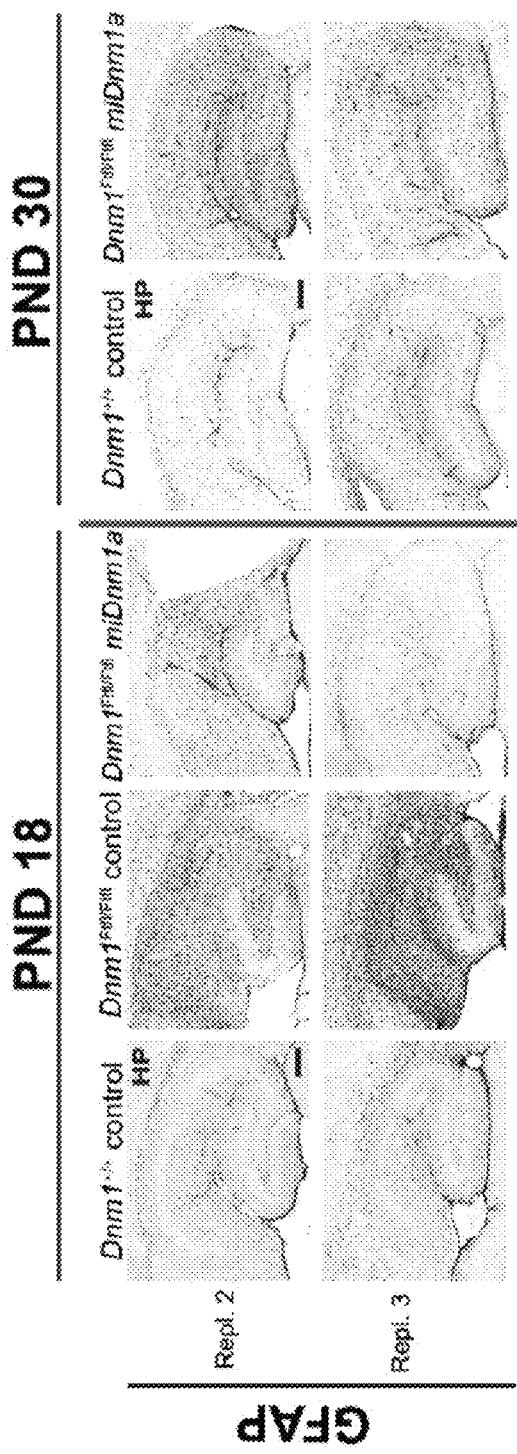
FIG. 7A-B shows PND 18 and PND 30 cellular phenotypes images (GFAP and FJC; two other representative replicate sets; related to FIG. 6A-D). A) Control-injected Dnm1$^{Ftfl/Ftfl}$ mice show increased hippocampal GFAP which is absent from treated Dnm1$^{Ftfl/Ftfl}$ mice and Dnm1$^{+/+}$ controls at PND 18. At PND 30, treated Dnm1$^{Ftfl/Ftfl}$ mice show a significant increase in GFAP compared to Dnm1$^{+/+}$ controls. Scale bar correspond to 200 .Lm. B) Control-injected Dnm1$^{Ftfl/Ftfl}$ mice show cell death in the hippocampal CA1. This phenotype is absent from treated Dnm1$^{Ftfl/Ftfl}$ mice and Dnm1$^{+/+}$ controls at PND 18. However, by PND 30 there is some noticeable cell death in the CA1 of treated mice compared to Dnm1$^{+/+}$ controls. Scale bar correspond to 100.Lm.
Figure 7B:
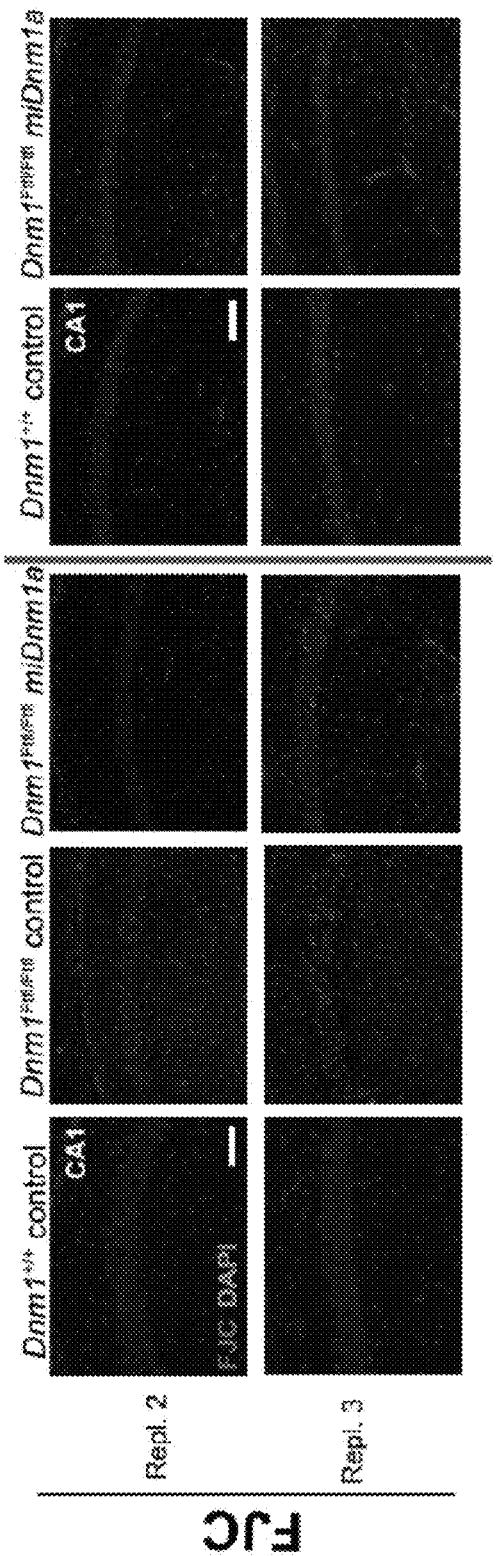

At PND 18, control-injected $Dnm1^{Ftfl/Ftfl}$ mice showed intense fibrillary gliosis (GFAP) in the hippocampus, specifically around CA1, compared to treated $Dnm1^{Ftfl/Ftfl}$ mice (p=0.018), indicative of a hippocampus under stress (FIG. 6A). In contrast, treated $Dnm1^{Ftfl/Ftfl}$ mice did not show gliosis and their hippocampi did not differ from wildtype controls (p>0.05; FIG. 6A, FIG. 7A). By the study endpoint at PND 30, surviving treated $Dnm1^{Ftfl/Ftfl}$ mice showed an increase in GFAP intensity in the hippocampus compared to treated and control-injected $Dnm1^{+/+}$ mice (p=0.0059 and p=0.0072 respectively; FIG. 6B, FIG. 7A). FJC labeling of control-injected $Dnm1^{Ftfl/Ftfl}$ mice revealed striking cellular degeneration in the hippocampus, and more so in the CA1 region compared to treated $Dnm1^{Ftfl/Ftfl}$ mice (p=0.015; FIG. 6C, FIG. 7B). This cell death phenotype was significantly diminished in treated $Dnm1^{Ftfl/Ftfl}$ mice which did not differ from control-injected $Dnm1^{Ftfl/Ftfl}$ mice (FIG. 6C). By the PND 30 endpoint, treated $Dnm1^{Ftfl/Ftfl}$ mice showed some cell death; however, not significantly more compared to treated and control-injected $Dnm1^{+/+}$ mice (FIG. 6D, FIG. 7B). These results revealed a susceptibility of the hippocampal neurons to $Dnm1^{Ftfl}$. Additionally, these results showed that miDnm1a treatment was successful at curbing or delaying gliosis and cellular degeneration in the hippocampus of $Dnm1^{Ftfl/Ftfl}$ mice at PND 18 and PND 30. (FIG. 6A-D, FIG. 7A-B).

Figure 8A:
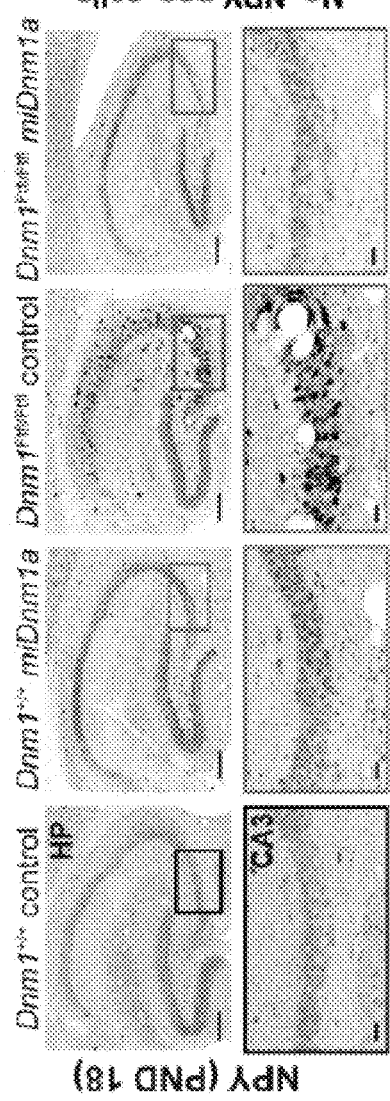
FIG. 8A-D shows miDnm1a treatment improves metabolic cellular activity at PND 18 until PND 30. A) Aberrant NPY expression was observed in the hippocampus and specifically in the CA3 of control-injected Dnm1$^{Ftfl/Ftfl}$ mice at PND 18; treatment with miDnm1a reverted this phenotype (p=0.0012). Treated Dnm1$^{Ftfl/Ftfl}$ mice did not differ from treated and control-injected Dnm1$^{+/+}$ mice (p>0.05). B) NPY expression varied amongst treated Dnm1$^{Ftfl/Ftfl}$ mice at PND 30. However, treated Dnm1$^{Ftfl/Ftfl}$ mice trended toward significance compared to treated Dnm1$^{+/+}$ mice (p=0.057) and control-injected Dnm1$^{+/+}$ mice (p=0.074). C) At PND18 c-Fos staining showed increased neuronal activation in the hippocampal CA3 of control-injected Dnm1$^{Ftfl/Ftfl}$ mice which was significantly diminished in treated Dnm1$^{Ftfl/Ftfl}$ mice (p<0.00001). Treated Dnm1$^{Ftfl/Ftfl}$ mice did not differ from Dnm1$^{+/+}$ controls (p>0.05). D) By PND 30, there was a modest increase in neuronal activation in the hippocampus, specifically in the CA3 region, of treated Dnm1$^{Ftfl/Ftfl}$ mice compared to Dnm1$^{+/+}$ controls, but this increase was not significant (p>0.05). All images (A-D) were taken at 10× magnification. Scale bar of entire hippocampus represents 200 μm and ROI scale bar represents 20 μm. Analyses were executed using the Poisson overdispersion option in the GMLJ module of Jamovi's software. 3-5 mice were used in these analysis and data are reported as mean±SEM. See also FIG. 9A-B.
Figure 8B:
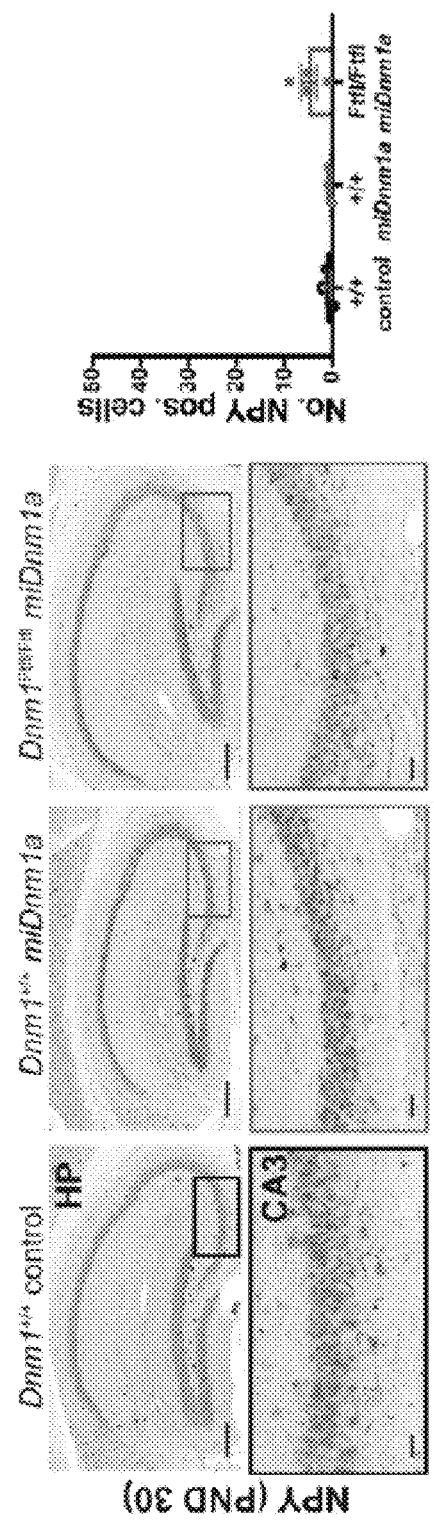
Figure 8C:
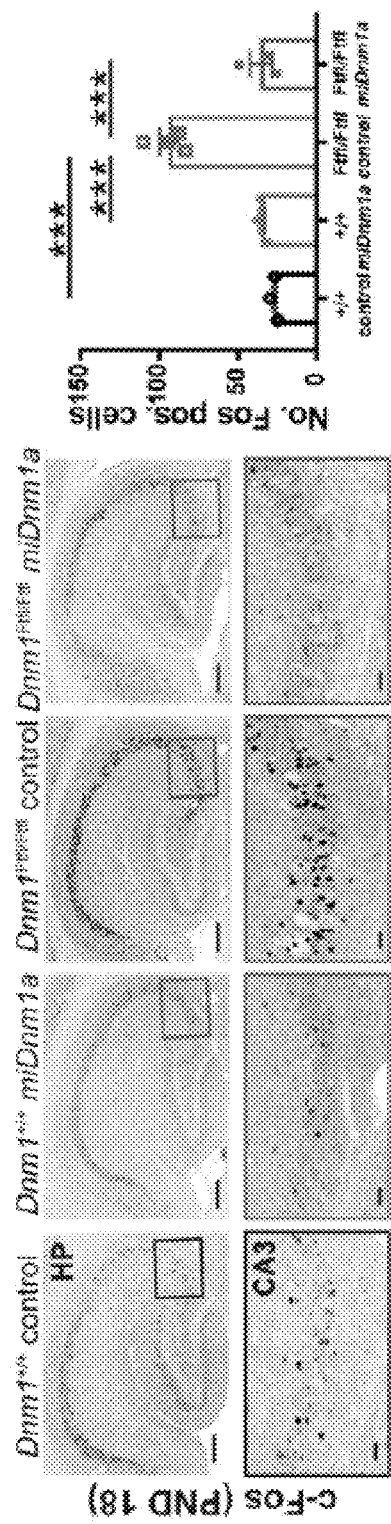
Figure 8D:
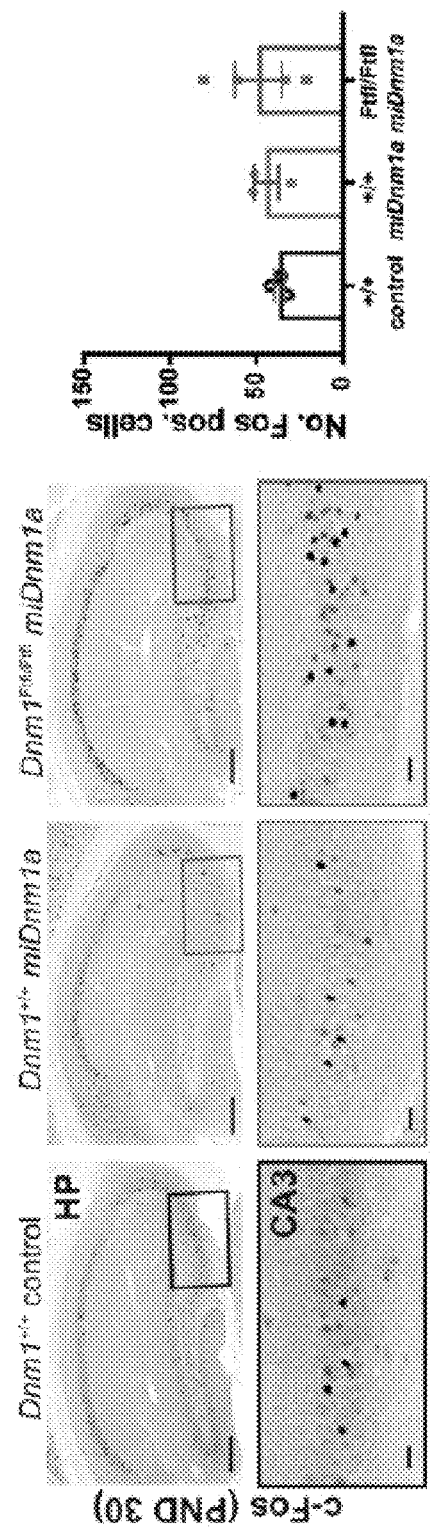
Figure 9A:
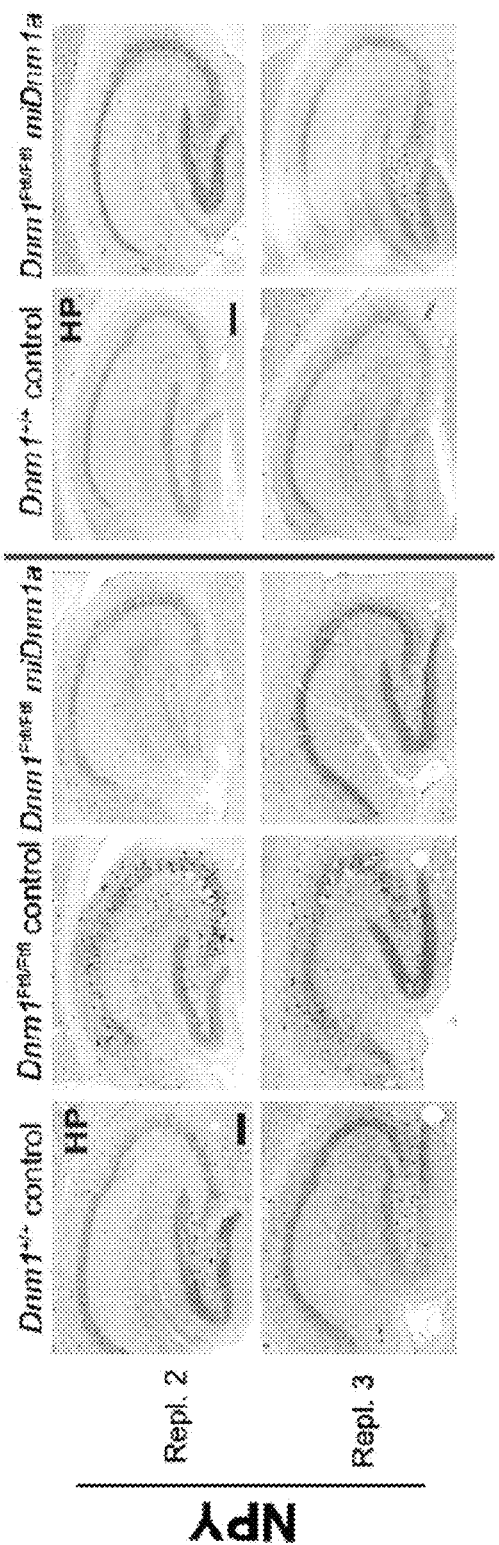
FIG. 9A-B shows PND 18 and PND 30 cellular phenotypes images (NPY and c-Fos; two other representative replicate sets; related to FIG. 8A-D). A) Dnm1$^{Ftfl/Ftfl}$ treated mice show a decrease of NPY+ cells in the hippocampus at PND 18 and PND 30 compared to control-injected Dnm1$^{Ftfl/Ftfl}$ mice. By PND 30 treated mice start to show increased NPY compared to Dnm1$^{+/+}$ controls in the CA3. B) Treated Dnm1$^{Ftfl/Ftfl}$ mice show decrease in c-Fos compared to control-injected Dnm1$^{Ftfl/Ftfl}$ mice at PND 18. By PND 30 treated mice show variable increase in hippocampal c-Fos expression compared to Dnm1$^{+/+}$ mice. Scale bars correspond to 200 μm.
Figure 9B:
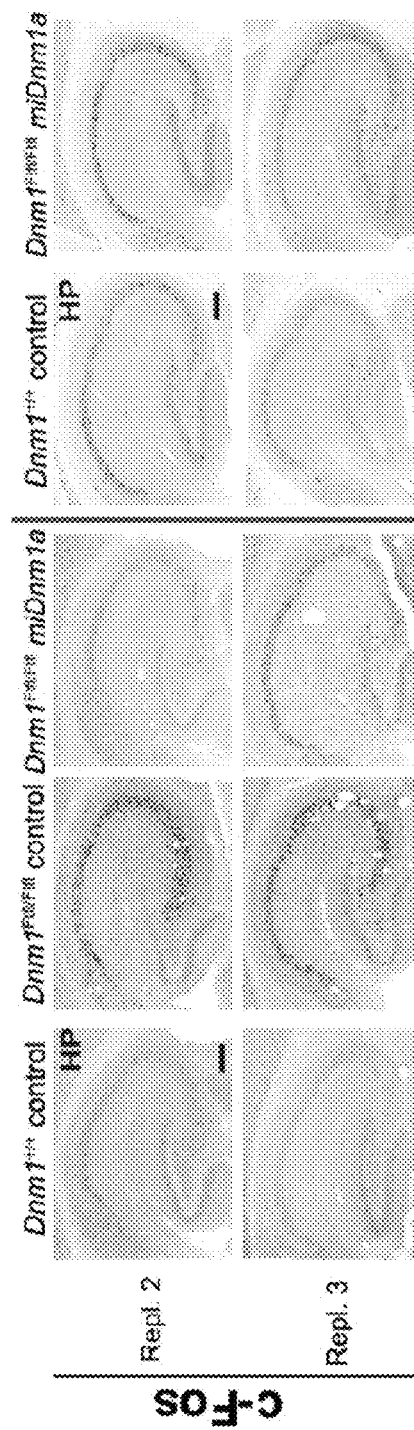

Given the increased gliosis and cellular degeneration observed in the hippocampus of control-injected $Dnm1^{Ftfl/Ftfl}$ mice, hippocampal involvement was further examined by using cellular footprints of metabolic activity typically associated with recurrent limbic seizure behavior. Neuropeptide Y (NPY) was examined, as upregulation of NPY in the hippocampus is a known method of evidencing hyperexcitability in rodent models of epilepsy. Aberrant cellular NPY expression was observed in the hippocampal *cornu ammonis* areas, specifically in CA3, of control-injected $Dnm1^{Ftfl/Ftfl}$ mice compared to treated $Dnm1^{Ftfl/Ftfl}$ mice at PND 18 (p=0.0012; FIG. 8A, FIG. 9A). Treated $Dnm1^{Ftfl/Ftfl}$ mice, however, showed NPY expression similar to treated and control-injected $Dnm1^{+/+}$ mice at PND 18 (p>0.05; FIG. 8A, FIG. 9A). By PND 30, treated $Dnm1^{Ftfl/Ftfl}$ mice still did not differ from treated and control-injected $Dnm1^{+/+}$ mice, although treated $Dnm1^{Ftfl/Ftfl}$ mice tended to have more aberrant $NPY^+$ cells in the CA3 (p>0.05; FIG. 8B, FIG. 9A). Additionally, immunostaining for the immediate early gene marker of neuronal activity, c-Fos, was also performed. A significant increase in c-$Fos^+$ cells in the hippocampus was found, specifically in the CA3 of control-injected $Dnm1^{Ftfl/Ftfl}$ mice (FIG. 8C; FIG. 9B). In contrast, this increased neuronal activity was abated in treated $Dnm1^{Ftfl/Ftfl}$ mice at PND 18 (p<0.00001) and persisted until PND 30 (FIG. 8C-D, FIG. 9B). Moreover, treated $Dnm1^{Ftfl/Ftfl}$ mice did not differ from treated and control-injected $Dnm1^{+/+}$ mice at PND 18 or PND 30 (p>0.05; FIG. 8C-D, FIG. 9B). These results suggest that miDnm1a treatment decreased the abnormal cellular metabolic activity of $Dnm1^{Ftfl/Ftfl}$ mice.

Overall, unlike control-injected $Dnm1^{Ftfl/Ftfl}$ mice, treated $Dnm1^{Ftfl/Ftfl}$ mice showed a decrease in gliosis, cell death, and aberrant neuronal activity at PND 18 which persisted and led to their survival until the PND 30 endpoint. These results together show that miDnm1a treatment diminished the cellular pathology associated with the $Dnm1^{Ftfl}$ mutation.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

We claim:

1. A nucleic acid comprising
   (a) a polynucleotide sequence comprising at least 82%, 83%, 84%, 85%, 86%, 87%, 88%, 89%, 90%, 91%, 92%, 93%, 94%, 95%, 96%, 97%, 98%, 99%, or 100% identity to the dynamin-1 (DNM1) artificial inhibitory RNA-encoding polynucleotide sequence set forth in any one of SEQ ID NOs: 1-17;
   (b) a polynucleotide sequence encoding a DNM1 artificial inhibitory RNA comprising the artificial inhibitory RNA polynucleotide sequence set forth in any one of SEQ ID NOs: 18-34; or
   (c) a polynucleotide sequence encoding a mature DNM1 antisense guide strand comprising the polynucleotide sequence set forth in any one of SEQ ID NO: 35-51.

2. The nucleic acid of claim 1, wherein
   (a) the polynucleotide sequence comprises at least 85% identity to the dynamin-1 (DNM1) artificial inhibitory RNA-encoding polynucleotide sequence set forth in any one of SEQ ID NOs: 1-17.

3. The nucleic acid of claim 1, wherein
   (a) the polynucleotide sequence comprises at least 90% identity to the dynamin-1 (DNM1) artificial inhibitory RNA-encoding polynucleotide sequence set forth in any one of SEQ ID NOs: 1-17.

4. The nucleic acid of claim 1, wherein
   (a) the polynucleotide sequence comprises at least 95% identity to the dynamin-1 (DNM1) artificial inhibitory RNA-encoding polynucleotide sequence set forth in any one of SEQ ID NOs: 1-17.

5. The nucleic acid of claim 1, wherein
   (a) the polynucleotide sequence comprises at least 98% identity to the dynamin-1 (DNM1) artificial inhibitory RNA-encoding polynucleotide sequence set forth in any one of SEQ ID NOs: 1-17.

6. The nucleic acid of claim 1, wherein
   (a) the polynucleotide sequence comprises the dynamin-1 (DNM1) artificial inhibitory RNA-encoding polynucleotide sequence set forth in any one of SEQ ID NOs: 1-17.

7. A viral vector comprising the nucleic acid of claim 1 or a combination of any one or more thereof.

8. The viral vector of claim 7, wherein the viral vector is an adeno-associated virus (AAV), adenovirus, lentivirus, retrovirus, poxvirus, baculovirus, herpes simplex virus, vaccinia virus, or a synthetic virus.

9. The viral vector of claim 8, wherein the viral vector is an AAV.

10. The viral vector of claim 9, wherein the AAV lacks rep and cap genes.

11. The viral vector of claim 10, wherein the AAV is a recombinant AAV (rAAV) or a self-complementary recombinant AAV (scAAV).

12. The viral vector of claim 9, wherein the AAV has a capsid serotype of: AAV-1, AAV-2, AAV-3, AAV-4, AAV-5, AAV-6, AAV-7, AAV-8, AAV-9, AAV-10, AAV-11, AAV-12, AAV-13, AAV-anc80, or AAV rh.74.

13. The viral vector of claim 12, wherein the AAV has a capsid serotype of AAV-9.

14. The viral vector of claim 9, wherein the AAV is a pseudotyped AAV.

15. The viral vector of claim 14, wherein the AAV is AAV2/8 or AAV2/9.

16. The viral vector of claim 7, wherein expression of the nucleic acid encoding the DNM1 artificial inhibitory RNA is under the control of a U6 promoter.

17. A composition comprising the nucleic acid of claim 1 and a pharmaceutically acceptable carrier.

18. The composition of claim 17, wherein expression of the nucleic acid encoding the DNM1 artificial inhibitory RNA is under the control of a U6 promoter.

19. A composition comprising the nucleic acid of claim 2 and a pharmaceutically acceptable carrier.

20. A composition comprising the nucleic acid of claim 3 and a pharmaceutically acceptable carrier.

21. A composition comprising the nucleic acid of claim 4 and a pharmaceutically acceptable carrier.

22. A composition comprising the nucleic acid of claim 5 and a pharmaceutically acceptable carrier.

23. A composition comprising the nucleic acid of claim 6 and a pharmaceutically acceptable carrier.

24. A composition comprising the viral vector of claim 7 and a pharmaceutically acceptable carrier.

25. A method of delivery to a neuron with a dynamin-1 (DNM1) gene, the method comprising administering to a subject with the neuron:
   (a) the nucleic acid of claim 1;
   (b) the vector of claim 7; or
   (c) the composition of claim 17.

* * * * *

SEQUENCE LISTING

```
<160> NUMBER OF SEQ ID NOS: 61

<210> SEQ ID NO 1
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1a-1 Full-length mouse miRNA sequence

<400> SEQUENCE: 1
ctcgagtgag cgatgtgtgg acatggtagt cagtctgtaa agccacagat gggactgact    60
accatgtcca cacactgcct actaga                                         86

<210> SEQ ID NO 2
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1a-4 Full-length mouse miRNA sequence

<400> SEQUENCE: 2
ctcgagtgag cgaaccatca gaaagtgtag tgaactgtaa agccacagat gggttcacta    60
cactttctga tggtgtgcct actaga                                         86

<210> SEQ ID NO 3
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Humanized miDNM1-10a-4 Full-length human miRNA
      sequence

<400> SEQUENCE: 3
ctcgagtgag cgaaccatca gaaagtgtag cgaactgtaa agccacagat gggttcgcta    60
cactttctga tggtgtgcct actaga                                         86

<210> SEQ ID NO 4
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-71 Full-length human miRNA sequence

<400> SEQUENCE: 4
ctcgagtgag cgaccagtat caagtgtgtg gatactgtaa agccacagat gggtatccac    60
acacttgata ctgggtgcct actaga                                         86

<210> SEQ ID NO 5
<211> LENGTH: 86
<212> TYPE: DNA
<213> ORGANISM: Artificial Sequence
```

```
<220> FEATURE:
<223> OTHER INFORMATION: synthetic
<220> FEATURE:
<221> NAME/KEY: misc_feature
<223> OTHER INFORMATION: miDNM1-10a-72 Full-length human miRNA sequence

<400> SEQUENCE: 5
ctcgagtgag cgacagtatc aagtgtgtgg atatctgtaa agccacagat gggatatcca        60
cacacttgat actggtgcct actaga                                             86

<210> SEQ ID NO 6
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-104 Full-length human miRNA sequence

<400> SEQUENCE: 6
ctcgagtgag cgaagctcac agccaccatc agaactgtaa agccacagat gggttctgat        60
ggtggctgtg agctctgcct actaga                                             86

<210> SEQ ID NO 7
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-106 Full-length human miRNA sequence

<400> SEQUENCE: 7
ctcgagtgag cgactcacag ccaccatcag aaagctgtaa agccacagat gggctttctg        60
atggtggctg tgagctgcct actaga                                             86

<210> SEQ ID NO 8
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-3 Full-length human miRNA sequence

<400> SEQUENCE: 8
ctcgagtgag cgagggctg tttaccccag acatctgtaa agccacagat gggatgtctg         60
gggtaaacag ccccgtgcct actaga                                             86

<210> SEQ ID NO 9
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-24 Full-length human miRNA sequence

<400> SEQUENCE: 9
ctcgagtgag cgcggccttt gagaccattg tgaactgtaa agccacagat gggttcacaa        60
tggtctcaaa ggccatgcct actaga                                             86
```

```
<210> SEQ ID NO 10
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-25 Full-length human miRNA sequence

<400> SEQUENCE: 10
ctcgagtgag cgagcctttg agaccattgt gaaactgtaa agccacagat gggtttcaca    60
atggtctcaa aggcctgcct actaga                                        86

<210> SEQ ID NO 11
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-49 Full-length human miRNA sequence

<400> SEQUENCE: 11
ctcgagtgag cgacaggtga agaagatccg agaactgtaa agccacagat gggttctcgg    60
atcttcttca cctgctgcct actaga                                        86

<210> SEQ ID NO 12
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-72 Full-length human miRNA sequence

<400> SEQUENCE: 12
ctcgagtgag cgagtgtctc aagtgtgtgg acatctgtaa agccacagat gggatgtcca    60
cacacttgag acacgtgcct actaga                                        86

<210> SEQ ID NO 13
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-101 Full-length human miRNA sequence

<400> SEQUENCE: 13
ctcgagtgag cgccggagct aatcagcacc gttactgtaa agccacagat gggtaacggt    60
gctgattagc tccgatgcct actaga                                        86

<210> SEQ ID NO 14
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-102 Full-length human miRNA sequence
```

<400> SEQUENCE: 14
ctcgagtgag cgaggagcta atcagcaccg ttagctgtaa agccacagat gggctaacgg    60
tgctgattag ctccgtgcct actaga                                          86

<210> SEQ ID NO 15
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-103 Full-length human miRNA sequence

<400> SEQUENCE: 15
ctcgagtgag cgagagctaa tcagcaccgt tagactgtaa agccacagat gggtctaacg    60
gtgctgatta gctcctgcct actaga                                          86

<210> SEQ ID NO 16
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-116 Full-length human miRNA sequence

<400> SEQUENCE: 16
ctcgagtgag cgcccgttag acagtgcacc aagactgtaa agccacagat gggtcttggt    60
gcactgtcta acggttgcct actaga                                          86

<210> SEQ ID NO 17
<211> LENGTH: 86
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-117 Full-length human miRNA sequence

<400> SEQUENCE: 17
ctcgagtgag cgacgttaga cagtgcacca agaactgtaa agccacagat gggttcttgg    60
tgcactgtct aacggtgcct actaga                                          86

<210> SEQ ID NO 18
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1a-1 Full-length mouse miRNA sequence

<400> SEQUENCE: 18
cucgagugag cgaugugugg acauggauagu cagucuguaa agccacagau gggacugacu    60
accaugucca cacacugccu acuaga                                          86

<210> SEQ ID NO 19
<211> LENGTH: 86
<212> TYPE: RNA

```
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1a-4 Full-length mouse miRNA sequence

<400> SEQUENCE: 19
cucgagugag cgaaccauca gaaaguguag ugaacuguaa agccacagau ggguucacua    60
cacuuucuga uggugugccu acuaga                                         86

<210> SEQ ID NO 20
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Humanized miDNM1-10a-4 Full-length human miRNA
      sequence

<400> SEQUENCE: 20
cucgagugag cgaaccauca gaaaguguag cgaacuguaa agccacagau ggguucgcua    60
cacuuucuga uggugugccu acuaga                                         86

<210> SEQ ID NO 21
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-71 Full-length human miRNA sequence

<400> SEQUENCE: 21
cucgagugag cgaccaguau caagugugug gauacuguaa agccacagau ggguauccac    60
acacuugaua cugggugccu acuaga                                         86

<210> SEQ ID NO 22
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-72 Full-length human miRNA sequence

<400> SEQUENCE: 22
cucgagugag cgacaguauc aagugugugg auaucuguaa agccacagau gggauaucca    60
cacacuugau acuggugccu acuaga                                         86

<210> SEQ ID NO 23
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-104 Full-length human miRNA sequence

<400> SEQUENCE: 23
cucgagugag cgaagcucac agccaccauc agaacuguaa agccacagau ggguucugau    60
```

```
gguggcugug agcucugccu acuaga                                          86

<210> SEQ ID NO 24
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-106 Full-length human miRNA sequence

<400> SEQUENCE: 24
cucgagugag cgacucacag ccaccaucag aaagcuguaa agccacagau gggcuuucug     60
augguggcug ugagcugccu acuaga                                          86

<210> SEQ ID NO 25
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-3 Full-length human miRNA sequence

<400> SEQUENCE: 25
cucgagugag cgaggggcug uuuaccccag acaucuguaa agccacagau gggaugucug     60
ggguaaacag ccccgugccu acuaga                                          86

<210> SEQ ID NO 26
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-24 Full-length human miRNA sequence

<400> SEQUENCE: 26
cucgagugag cgcggccuuu gagaccauug ugaacuguaa agccacagau ggguucacaa     60
uggucucaaa ggccaugccu acuaga                                          86

<210> SEQ ID NO 27
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-25 Full-length human miRNA sequence

<400> SEQUENCE: 27
cucgagugag cgagccuuug agaccauugu gaaacuguaa agccacagau ggguuucaca     60
auggucucaa aggccugccu acuaga                                          86

<210> SEQ ID NO 28
<211> LENGTH: 86
<212> TYPE: RNA
<213> ORGANISM: Artificial Sequence
<220> FEATURE:
<223> OTHER INFORMATION: synthetic
<220> FEATURE:
```

```
<221> NAME/KEY: misc_feature
<223> OTHER INFORMATION: miDNM1-10b-49 Full-length human miRNA sequence

<400> SEQUENCE: 28
cucgagugag cgacagguga agaagauccg agaacuguaa agccacagau ggguucucgg    60
aucuucuuca ccugcugccu acuaga                                         86

<210> SEQ ID NO 29
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-72 Full-length human miRNA sequence

<400> SEQUENCE: 29
cucgagugag cgagugucuc aagugugugg acaucuguaa agccacagau gggaugucca    60
cacacuugag acacgugccu acuaga                                         86

<210> SEQ ID NO 30
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-101 Full-length human miRNA sequence

<400> SEQUENCE: 30
cucgagugag cgccggagcu aaucagcacc guuacuguaa agccacagau ggguaacggu    60
gcugauuagc uccgaugccu acuaga                                         86

<210> SEQ ID NO 31
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-102 Full-length human miRNA sequence

<400> SEQUENCE: 31
cucgagugag cgaggagcua aucagcaccg uuagcuguaa agccacagau gggcuaacgg    60
ugcugauuag cuccgugccu acuaga                                         86

<210> SEQ ID NO 32
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-103 Full-length human miRNA sequence

<400> SEQUENCE: 32
cucgagugag cgagagcuaa ucagcaccgu uagacuguaa agccacagau gggucuaacg    60
gugcugauua gcuccugccu acuaga                                         86

<210> SEQ ID NO 33
```

```
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-116 Full-length human miRNA sequence

<400> SEQUENCE: 33
cucgagugag cgcccguuag acagugcacc aagacuguaa agccacagau gggucuuggu    60
gcacugucua acgguugccu acuaga                                        86

<210> SEQ ID NO 34
<211> LENGTH: 86
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-117 Full-length human miRNA sequence

<400> SEQUENCE: 34
cucgagugag cgacguuaga cagugcacca agaacuguaa agccacagau ggguucuugg    60
ugcacugucu aacggugccu acuaga                                        86

<210> SEQ ID NO 35
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1a-1 Mature antisense sequence

<400> SEQUENCE: 35
acugacuacc auguccacac ac                                            22

<210> SEQ ID NO 36
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1a-4 Mature antisense sequence

<400> SEQUENCE: 36
uucacuacac uuucugaugg ug                                            22

<210> SEQ ID NO 37
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Humanized miDNM1-10a-4 Mature antisense
      sequence

<400> SEQUENCE: 37
uucgcuacac uuucugaugg ug                                            22
```

```
<210> SEQ ID NO 38
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-71 Mature antisense sequence

<400> SEQUENCE: 38
uauccacaca cuugauacug gg                                              22

<210> SEQ ID NO 39
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-72 Mature antisense sequence

<400> SEQUENCE: 39
auauccacac acuugauacu gg                                              22

<210> SEQ ID NO 40
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-104 Mature antisense sequence

<400> SEQUENCE: 40
uucugauggu ggcugugagc uc                                              22

<210> SEQ ID NO 41
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10a-106 Mature antisense sequence

<400> SEQUENCE: 41
cuuucugaug guggcuguga gc                                              22

<210> SEQ ID NO 42
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-3 Mature antisense sequence

<400> SEQUENCE: 42
augucugggg uaaacagccc cg                                              22

<210> SEQ ID NO 43
<211> LENGTH: 22
<212> TYPE: RNA
<213> ORGANISM: Artificial Sequence
```

```
<220> FEATURE:
<223> OTHER INFORMATION: synthetic
<220> FEATURE:
<221> NAME/KEY: misc_feature
<223> OTHER INFORMATION: miDNM1-10b-24 Mature antisense sequence

<400> SEQUENCE: 43
uucacaaugg ucucaaaggc ca                                              22

<210> SEQ ID NO 44
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-25 Mature antisense sequence

<400> SEQUENCE: 44
uuucacaaug gucucaaagg cc                                              22

<210> SEQ ID NO 45
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-49 Mature antisense sequence

<400> SEQUENCE: 45
uucucggauc uucuucaccu gc                                              22

<210> SEQ ID NO 46
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-72 Mature antisense sequence

<400> SEQUENCE: 46
auguccacac acuugagaca cg                                              22

<210> SEQ ID NO 47
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-101 Mature antisense sequence

<400> SEQUENCE: 47
uaacggugcu gauuagcucc ga                                              22

<210> SEQ ID NO 48
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
```

<223> OTHER INFORMATION: miDNM1-10b-102 Mature antisense sequence

<400> SEQUENCE: 48
cuaacggugc ugauuagcuc cg                                              22

<210> SEQ ID NO 49
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-103 Mature antisense sequence

<400> SEQUENCE: 49
ucuaacggug cugauuagcu cc                                              22

<210> SEQ ID NO 50
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-116 Mature antisense sequence

<400> SEQUENCE: 50
ucuuggugca cugucuaacg gu                                              22

<210> SEQ ID NO 51
<211> LENGTH: 22
<212> TYPE: RNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: miDNM1-10b-117 Mature antisense sequence

<400> SEQUENCE: 51
uucuuggugc acugucuaac gg                                              22

<210> SEQ ID NO 52
<211> LENGTH: 139
<212> TYPE: DNA
<213> ORGANISM: Homo sapiens

<400> SEQUENCE: 52
gacgggcctc ttcacacctg acctcgcttt tgaagccaca gtgaaaaagc aggtgcagaa      60
gctcaaagag cccagtatca agtgtgtgga tatggtagtc agtgagctca cagccaccat     120
cagaaagtgt agcgaaaag                                                  139

<210> SEQ ID NO 53
<211> LENGTH: 139
<212> TYPE: DNA
<213> ORGANISM: Homo sapiens

<400> SEQUENCE: 53 aacgggctg tttaccccag acatggcctt tgagaccatt gtgaaaaagc aggtgaagaa       60
gatccgagaa ccgtgtctca agtgtgtgga catggttatc tcggagctaa tcagcaccgt    120
tagacagtgc accaagaag                                                  139

<210> SEQ ID NO 54
<211> LENGTH: 138
<212> TYPE: DNA
<213> ORGANISM: Mus musculus

<400> SEQUENCE: 54
gacgggcctc ttcacacctg acctcgcttt tgaagccaca gtgaaaaagc aggtgcagaa    60
gctcaaagag cccagtatca agtgtgtgga catggtagtc agtgaactca cgtccaccat   120
cagaaagtgt agtgaaaa                                                 138

<210> SEQ ID NO 55
<211> LENGTH: 139
<212> TYPE: DNA
<213> ORGANISM: Mus musculus

<400> SEQUENCE: 55
aacggggctc tttaccccag acatggcctt tgaaaccatt gtgaaaaagc aggtgaagaa    60
gattcgagag ccgtgtctca agtgtgtgga catggttatc tcggagctaa tcagcacggt   120
tagacagtgc accaagaag                                                139

<210> SEQ ID NO 56
<211> LENGTH: 20
<212> TYPE: DNA
<213> ORGANISM: Artificial Sequence
<220> FEATURE:
<223> OTHER INFORMATION: synthetic

<400> SEQUENCE: 56
ctcgcttttg aagccacagt                                                20

<210> SEQ ID NO 57
<211> LENGTH: 20
<212> TYPE: DNA
<213> ORGANISM: Artificial Sequence
<220> FEATURE:
<223> OTHER INFORMATION: synthetic

<400> SEQUENCE: 57
gagtgcaggt ggtagtcttt                                                20

<210> SEQ ID NO 58
<211> LENGTH: 20
<212> TYPE: DNA
<213> ORGANISM: Artificial Sequence
<220> FEATURE:
<223> OTHER INFORMATION: synthetic

<400> SEQUENCE: 58
ggcctttgaa accattgtga                                                20

<210> SEQ ID NO 59
<211> LENGTH: 20
<212> TYPE: DNA
<213> ORGANISM: Artificial Sequence
<220> FEATURE:
<223> OTHER INFORMATION: synthetic

<400> SEQUENCE: 59
agtcgtgcca atctgtcacg                                                20

<210> SEQ ID NO 60
<211> LENGTH: 24

```
<212> TYPE: DNA
<213> ORGANISM: Artificial Sequence
<220> FEATURE:
<223> OTHER INFORMATION: synthetic

<400> SEQUENCE: 60
cctctctgtc cacttgtagc catt                                              24

<210> SEQ ID NO 61
<211> LENGTH: 24
<212> TYPE: DNA
<213> ORGANISM: Artificial Sequence
<220> FEATURE:
<223> OTHER INFORMATION: synthetic

<400> SEQUENCE: 61
tccaagatca ctcgtagtgg gtca                                              24
```